United States Patent
Poudel et al.

(10) Patent No.: US 11,911,483 B2
(45) Date of Patent: *Feb. 27, 2024

(54) MODIFIED SELF-IMMOLATING MOIETIES FOR USE IN PRODRUGS AND CONJUGATES AND METHODS OF USING AND MAKING

(71) Applicant: BRISTOL-MYERS SQUIBB COMPANY, Princeton, NJ (US)

(72) Inventors: Yam B. Poudel, Fremont, CA (US); Sanjeev Gangwar, Foster City, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 316 days.

This patent is subject to a terminal disclaimer.

(21) Appl. No.: 17/126,555

(22) Filed: Dec. 18, 2020

(65) Prior Publication Data

US 2021/0113706 A1   Apr. 22, 2021

Related U.S. Application Data

(63) Continuation of application No. 16/425,596, filed on May 29, 2019, now Pat. No. 10,898,578.

(60) Provisional application No. 62/677,307, filed on May 29, 2018.

(51) Int. Cl.
| | |
|---|---|
| A61K 47/65 | (2017.01) |
| A61K 47/64 | (2017.01) |
| A61K 47/68 | (2017.01) |
| A61P 35/00 | (2006.01) |
| A61K 45/06 | (2006.01) |

(52) U.S. Cl.
CPC ............. *A61K 47/65* (2017.08); *A61K 45/06* (2013.01); *A61K 47/6425* (2017.08); *A61K 47/6865* (2017.08); *A61P 35/00* (2018.01)

(58) Field of Classification Search
CPC .... A61K 47/65; A61K 45/06; A61K 47/6425; A61K 47/6865; A61K 47/6851; A61K 47/6809; A61K 47/6889; A61P 35/00
See application file for complete search history.

(56) References Cited

U.S. PATENT DOCUMENTS

| | | | |
|---|---|---|---|
| 6,214,345 B1 | 4/2001 | Firestone | |
| 7,091,186 B2 | 8/2006 | Senter | |
| 7,375,078 B2 | 5/2008 | Feng | |
| 7,691,962 B2 | 4/2010 | Boyd | |
| 7,989,434 B2 | 8/2011 | Feng | |
| 8,039,273 B2 | 10/2011 | Jeffrey | |
| 8,828,678 B2 | 9/2014 | Szczepanik et al. | |
| 9,089,614 B2 | 7/2015 | Lin | |
| 10,898,578 B2 * | 1/2021 | Poudel | A61K 47/6865 |
| 2016/0184451 A1 | 6/2016 | Kim | |
| 2017/0095576 A1 | 4/2017 | Kim | |
| 2017/0247412 A1 | 8/2017 | Burke | |

FOREIGN PATENT DOCUMENTS

| | | | |
|---|---|---|---|
| CA | 104587 A1 | 4/1907 | |
| CA | 3027103 A1 | 12/2017 | |
| CN | 104587487 A | 1/2018 | |
| WO | 8101145 A1 | 4/1981 | |
| WO | 2004020400 A1 | 3/2004 | |
| WO | 2007103288 A2 | 9/2007 | |
| WO | WO2016040684 * | 3/2016 | ............... C07K 7/02 |
| WO | 2017214335 A1 | 12/2017 | |
| WO | 2017214458 A2 | 12/2017 | |
| WO | 2017214462 A2 | 12/2017 | |

OTHER PUBLICATIONS

Alouane et al., Self-Immolative Spacers: Kinetic Aspects, Structure-Property Relationships, and Applications, 2015, 7492_7509, 54, Angewandte Reviews.
Carl et al., A Novel Connector Linkage Applicable in Prodrug Design, 1981, 479_480, 24_5, Journal of Medicinal Chemistry.
Doronina et al., Novel Peptide Linkers for Highly Potent Antibody-Auristatin Conjugate, 2008, 1960_1963, 19, Bioconjugate Chemistry.
Dorywalska et al., Molecular Basis of Valine-Citrulline-PABC Linker Instability in Site-Specific ADCs and Its Mitigation by Linker Design, 2016, 958_971, 15_5, Molecular Cancer Ther.
Dubowchik et al., Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity, 2002, 855_869, 13, Bioconjugate Chemistry.
Dubowchik et al., Cathepsin B_Sensitive Dipeptide Prodrugs. 1. a Model Study of . . . , 1998, 3341_3346, 8, Bioorgannic & Medicinal Chemistry Letters.

(Continued)

*Primary Examiner* — Marcela M Cordero Garcia
(74) *Attorney, Agent, or Firm* — Joseph F. Reidy; Yuan Chao

(57) ABSTRACT

Compounds represented by formula (I)

(I)

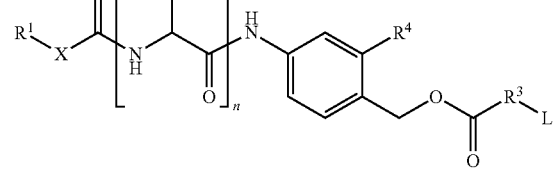

can be used to make antibody-drug conjugates. The conjugates so made are stable in both human and mouse serum, enabling the performance of pre-clinical studies using a mouse model.

6 Claims, 8 Drawing Sheets

(56) References Cited

OTHER PUBLICATIONS

Dubowchik et al., Cathepwin B_Sensitive Dipeptide Prodrugs. 2. Models of Anticancer Drug . . . , 1998, 3347_3352, 8, Bioorganic & Medicinal Chemistry Letters.

Gerber et al., The antibody-drug conjugate: an enabling modality for natural product-based cancer therapeutics, 2013, 625_639, 30, Nat. Prod. Rep.

International Search Report, Aug. 20, 2019, ISA_EP.

Jeffrey et al., Development and Properties of â-Glucuronide Linkers for Monoclonal Antibody-Drug Conjugates, 2006, 831_840, 17, Bioconjugate Chemistry.

Jourden et al., Investigation of self-immolative linkers in the design of hydrogen peroxide activated metalloprotein inhibitorsw, 2011, 7968_7970, 47, Chem Comm.

Machida et al., Allosterically Regulated Phosphatase Activity from Peptide-PNA Conjugates Folded Through Hybridization, 2016, 8595_8598, 55, Angewandte Chem Int.

Translation of CN104587487A, Novel Branched-Chain Co Necting Body Applied to Targeting Drug Delivery System, 2019, CN.

Zhang et al., An enzyme-activatable probe with a self-immolative linker for rapid and sensitive alkaline phosphatase detection and cell imaging through a cascade Reaction, 2015, 7031_7034, 51, Chem Comm.

Zhang et al., Design, Synt esis, and Biological Evaluation of New Cathepsin B-Sensitive Camptothecin Nanoparticles Equipped with a Novel Multifunctional Linker, 2016, 1267_1275, 27, Bioconjugate Chemistry.

Zhu et al., Maleimidation of dextran and the application in designing a dextran-camptothecin conjugate, 2018, 2818_2823, 8, RSC Advances.

\* cited by examiner

Scheme A

Scheme A (continued)

Scheme B

Scheme B (continued)

Scheme B (continued)

Scheme D

MODIFIED SELF-IMMOLATING MOIETIES FOR USE IN PRODRUGS AND CONJUGATES AND METHODS OF USING AND MAKING

CROSS-REFERENCE TO RELATED APPLICATIONS

This application is a continuation of application Ser. No. 16/425,596, filed May 29, 2019, which claims the benefit under 35 U.S.C. § 119(e) of U.S. Provisional Application Ser. No. 62/677,307, filed May 29, 2018; the disclosures of which are incorporated herein by reference.

BACKGROUND OF THE INVENTION

This disclosure relates to enzymatically activated self-immolating moieties, which have been modified to modulate their enzymatic activation, for use in prodrugs and conjugates.

Sometimes it is desirable to attach a peptide to a biologically active molecule to temporarily block the latter's activity until exposure to a protease enzyme cleaves the peptide bond and releases it in its unblocked, active form. The biologically active molecule can be a small molecule drug or a biologic, such as an antibody.

If the peptide is directly attached to the biologically active molecule, the latter can interfere with the protease's ability to cleave the peptide bond, for steric or other reason. If so, a self-immolating (SI) moiety can be interposed between the peptide and biologically active molecule. A commonly used SI moiety is a p-aminobenzyloxycarbonyl (PABC) group, whose mode of action is depicted below, where the biologically active molecule is an amine-containing one of the general formula $D-NH_2$, P is a peptide cleavable at dotted line (a) by a protease, and Y is an optionally present moiety that can serve different functions, as discussed below.

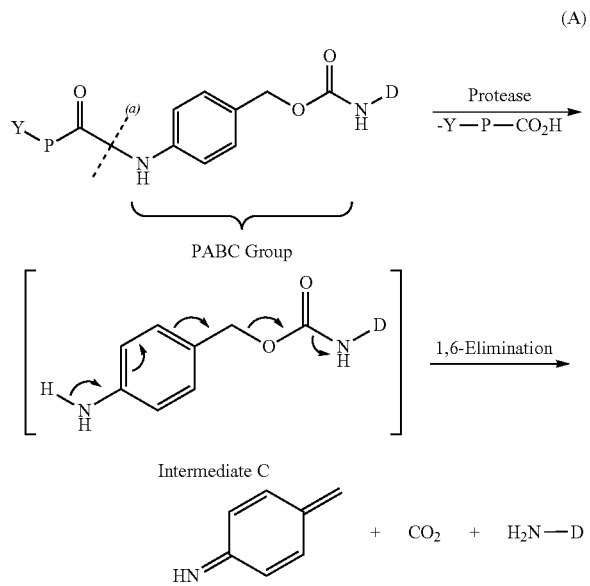

Protease cleavage of peptide P at dotted line (a) produces an intermediate C, which is unstable and spontaneously underdoes a self-immolation reaction (mechanistically, a 1,6-elimination) and decarboxylation to release $D-NH_2$. The PABC group provides a spatial separation between D and P to prevent the former from interfering with the protease's action, but yet is structured such that it itself does not interfere. See Carl et al. 1981a and Doronina et al. 2008. See also Alouane et al. for a general discussion on the use of SI moieties as spacers.

In a variation, the biologically active molecule can be D-OH—that is, an alcohol instead of an amine—released by an analogous mechanism. Where D-OH is a sufficiently good leaving group, the SI moiety can be simplified to a p-aminobenzyl alcohol (PABA) group, which self-immolates via the same 1,6-elimination reaction, except for the absence of decarboxylation.

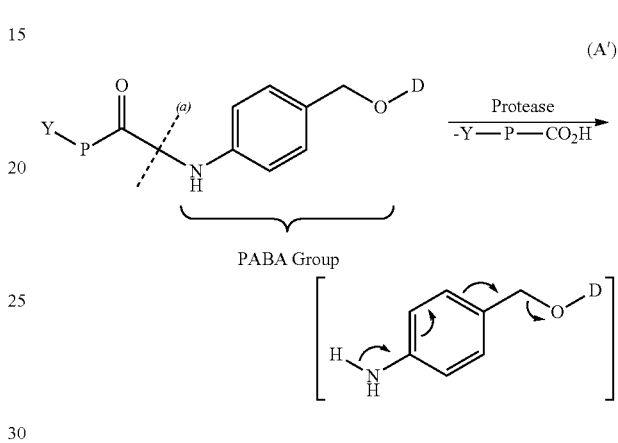

One embodiment of formula (A) is an antibody-drug conjugate ("ADC," also referred to as an immunoconjugate), for the targeted delivery of $D-NH_2$ to a site of intended action, such as a tumor. If so, Y represents an antibody and $D-NH_2$ is synonymously referred to as the therapeutic agent, warhead, or payload. For anti-cancer treatment, the antibody Y is selected such that its antigen is a tumor associated antigen—i.e., one that is uniquely or preferentially expressed by a cancer cell—so that antibody Y serves as a targeting agent leading the ADC to the cancer site.

If the antigen is located on the surface of a cancer cell, binding thereto by the ADC frequently leads to internalization of the antigen-ADC complex by endocytosis into the target cell. The ADC eventually finds its way into an organelle such as a lysosome. The sequence of peptide P is one that is a selective substrate for a lysosomal protease. Its cleavage by the protease liberates $D-NH_2$. While the ADC is circulating in the bloodstream, $D-NH_2$ is inactive because it remains attached to the antibody and peptide P is not a substrate for the proteases found in blood. For a review on ADCs, see Gerber et al. 2013.

In another embodiment, (A) can be a prodrug, in which $D-NH_2$ is held inactive due to its linkage to the PABC group. If the PABC group and peptide P are by themselves sufficient to block the activity of $D-NH_2$, then Y can be absent. Otherwise, Y can be present, to provide an additional blocking effect, in which case Y is referred to as blocking moiety. As Y does not perform a targeting function, selective release of $D-NH_2$ at site of intended action relies on designing peptide P such that it is selectively cleaved by an enzyme predominantly found at the site, compared to tissue elsewhere or in the blood.

Typically, the aromatic ring in a PABC or PABA moiety is an unsubstituted 1,4-phenylene ring, as shown above. However, there are disclosures of substituted rings. Electron withdrawing groups have been stated to accelerate the 1,6-elimination reaction. See, e.g., Boyd et al. 2010, Burke et al. 2017, Carl et al. 1981b, McDonagh et al. 2007, Senter et al. 2006, and Szczepanik et al. 2014.

There have also been disclosures of SI moieties in which the aromatic ring is an optionally substituted five- or six-membered heterocycle that can also undergo an 1,6-elimination reaction. See, e.g., Feng 2008 and 2011.

SI moieties in which an 1,6-elimination reaction is triggered by a reaction other than peptide bond cleavage are also known. Other triggering reactions can be cleavage of a glucuronide moiety, hydrolysis of a borate ester, hydrolysis of a phosphate, reduction of a nitro group to an amine, and reduction of an azide group to an amine, often mediated by an enzyme. For a review on diverse SI moieties and their properties, see Alouane et al. 2015. For specific disclosures on non-PABC or -PABA SI moieties, see, e.g., Jeffrey 2011, Jeffrey et al. 2006, Kim et al. 2016, Machida et al. 2016, Major et al. 2011 and Zhang et al. 2015.

A hydrophilic group has been attached to the benzylic position of a PABC group to improve solubility. Lin et al. 2016.

Full citations for the documents cited herein by first author or inventor and year are listed at the end of this specification.

BRIEF SUMMARY OF THE INVENTION

There are situations where it is desirable to modulate the proteolytic susceptibility of a peptide-PABC bond, either to prevent cleavage by a protease other than the intended activation protease or to modulate the rate of release of the biologically active molecule by the activating protease.

For an ADC or prodrug to be effective, cleavage of peptide P should not occur prematurely, for example while the ADC or prodrug is circulating in the blood system. For an internalized ADC, peptide P can be designed so that is specifically cleaved by a lysosomal enzyme, with cathepsin B being a preferred one. See Dubowchik et al. 1998a, 1998b, and 2002 and Firestone et al. 2001.

For a prodrug, the enzyme can be one that is more abundantly found in the extracellular environs of diseased tissue compare to healthy tissue, such as matriptase or matrix metalloproteinase. Absolute selectivity is difficult achieve, as blood contains its own complement of proteases, for which P could be a substrate.

In the preclinical evaluation of an ADC or prodrug candidate, its stability in human blood serum is initially evaluated. If it demonstrates the requisite stability, it becomes a viable candidate for further preclinical evaluation in animal models, usually a mouse model for reasons of expediency, as requiring less of the candidate material and less expensive to perform compared to models using primates or larger rodents. Also, mouse serum esterase activity is generally higher than that of human serum, so that an ADC that is stable in mouse serum can be expected to be stable in human serum.

The complement of proteases in mouse serum differs from that in human serum, meaning that an ADC or prodrug stable in human serum cannot be assumed to be stable in mouse serum. Hence, it is important to test a candidate ADC or prodrug for stability in mouse serum as well. If unstable there, then a mouse model is uninformative: one cannot tell if lack of efficacy or the occurrence of toxic side effects is attributable to premature release of the drug while in the blood stream or instability of the ADC per se.

Cathepsins—in particular cathepsin B—have been a preferred lysosomal activation enzyme in ADCs, as peptide sequences that are substrates for it are not substrates for proteases found in human blood serum. However, it has been observed that some ADCs designed for cleavage by cathepsin B, though stable in human serum, are unstable in mouse serum, due to the action of carboxyesterase C1 contained therein. Dorywalska et al. 2016. Such instability precludes the use of mouse models, making it difficult to evaluate drug candidate compounds in an animal model.

We have discovered that certain substituents on a PABC group, positioned ortho to the benzyloxycarbonyl group, can modulate the susceptibility to protease cleavage of a peptide moiety attached thereto, either preventing its cleavage by a protease that is not the intended activation protease or slowing down the rate of cleavage by the intended activation protease. In particular, SI moieties with the ortho-substituents retain their stability in human serum and show improved stability in mouse serum, but are still readily cleavable by cathepsin B.

In one embodiment there is provided a compound represented by formula (I)

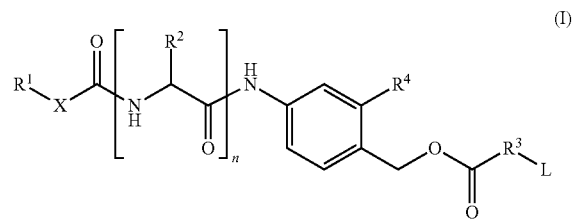

wherein $R^1$ is $C_1$-$C_5$ alkyl, $N_3$, OH, SH, $ONH_2$, $NH_2$, $CO_2H$,

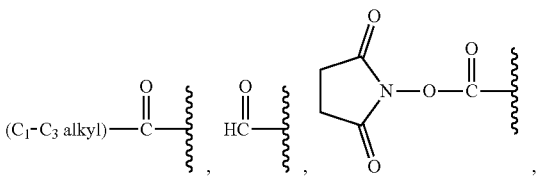

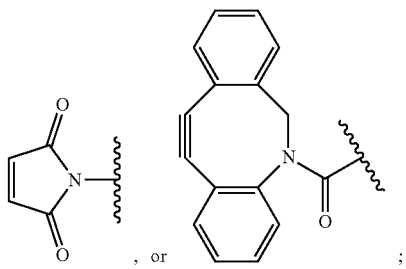

, or                        ;

$R^2$ is the side chain residue of an amino acid selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

n is 2, 3, 4, or 5;

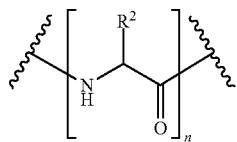

comprising a polypeptide whose bond to

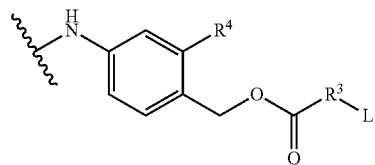

is cleavable by cathepsin B;
R³ is O, NH,

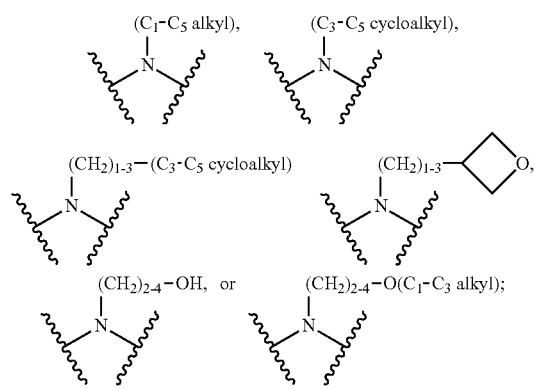

R⁴ is a moiety that substantially inhibits cleavage of the bond between

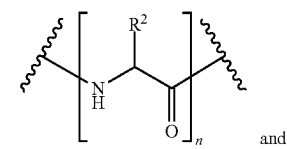
and
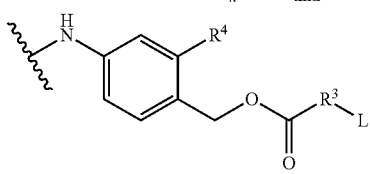

in mouse serum but does not substantially inhibit cleavage of the same bond by cathepsin B;
L is the residue of a bioactive molecule of the formula L-R³H; and
X is spacer group.

Compounds of formula (I) can be used to make ADCs, using a reactive R¹ group such as, by way of example and not limitation, NH₂, for conjugation to an antibody. Thus, in another embodiment, there is provided a conjugate represented by formula (II):

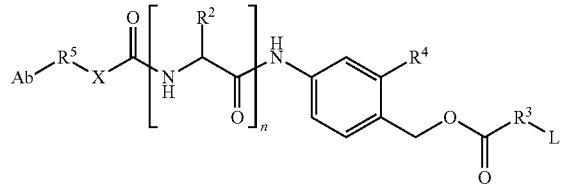

wherein
Ab is an antibody,
R² is the side chain residue of an amino acid selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;
n is 2, 3, 4, or 5;

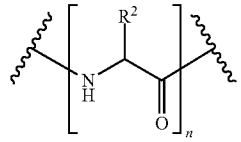

comprising a polypeptide whose bond to

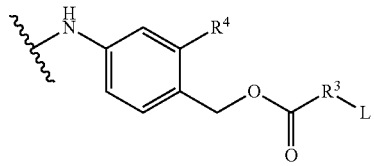

is cleavable by cathepsin B;
R³ is O, NH, (C₁-C₅ alkyl), (C₃-C₅ cycloalkyl),
(CH₂)₁₋₃—(C₃-C₅ cycloalkyl), (CH₂)₁₋₃-oxetanyl,
(CH₂)₂₋₄—OH, or (CH₂)₂₋₄—O(C₁-C₃ alkyl);

R⁴ is a moiety that substantially inhibits cleavage of the bond between

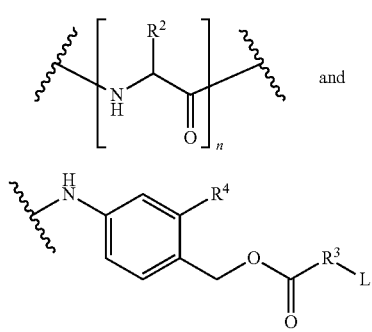

and in mouse serum but does not substantially inhibit cleavage of the same bond by cathepsin B;

$R^5$ is

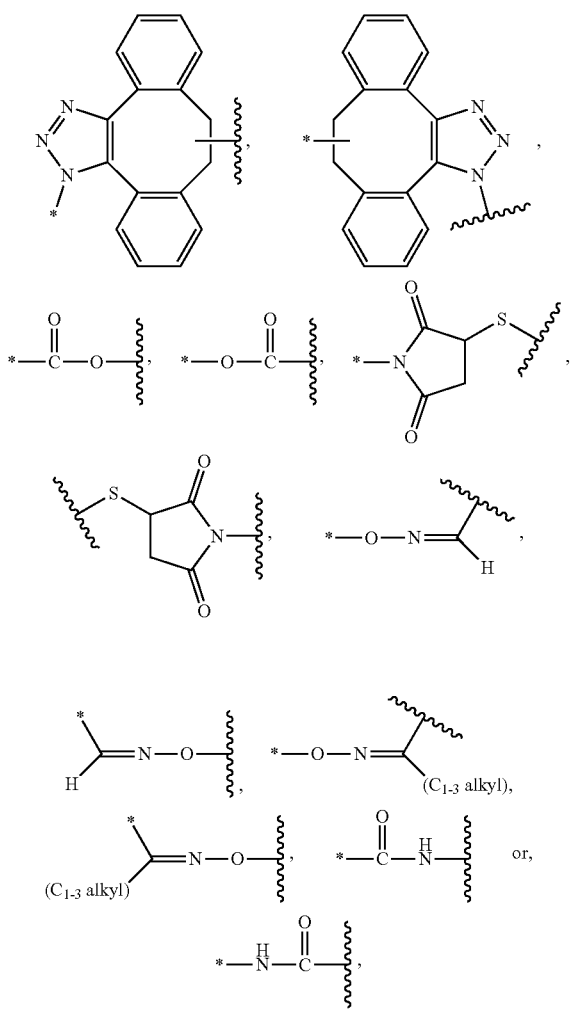

where the valence position of bonding to Ab is denoted by an asterisk and the valence position of bonding to X is denoted by a wavy line;

L is the residue of a bioactive molecule of the formula L-$R^3$H; and

X is spacer group.

Preferably, $R^4$ in formula (I) or (II) is

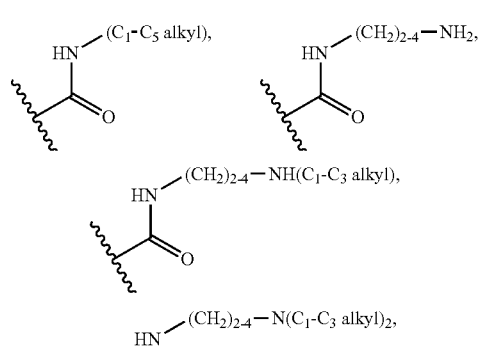

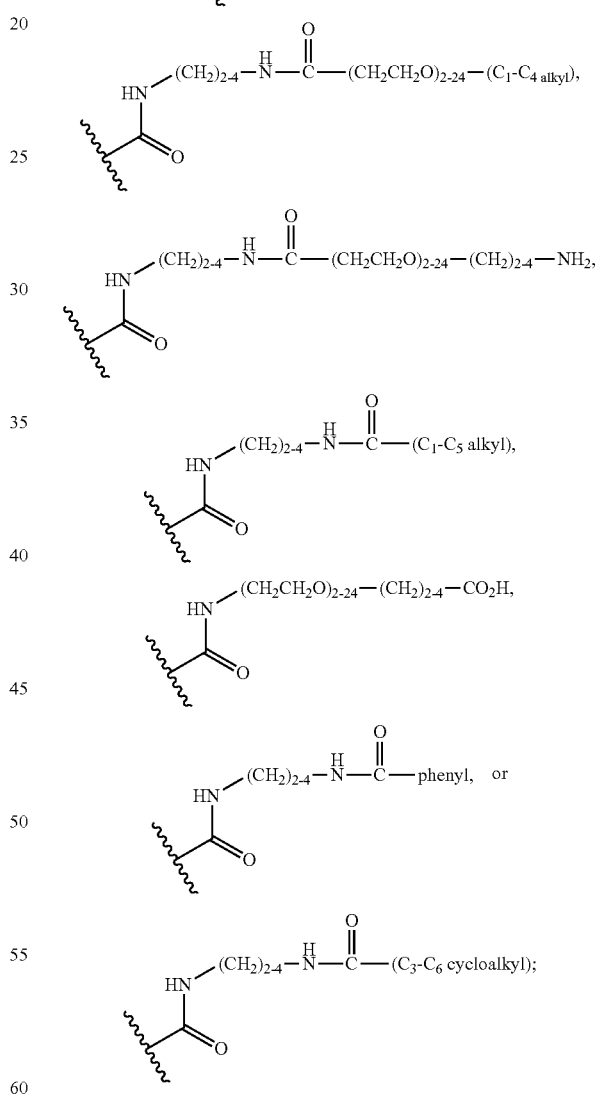

a phenyl or $C_3$-$C_6$ cycloalkyl group being optionally substituted with F, Cl, CN, $NO_2$, or $C_1$-$C_3$ alkyl.

In another embodiment, there is provided a method of making a conjugate represented by formula (II) comprising conjugating an antibody Ab with a compound of formula (I).

BRIEF DESCRIPTION OF THE DRAWING(S)

Figure 3A:
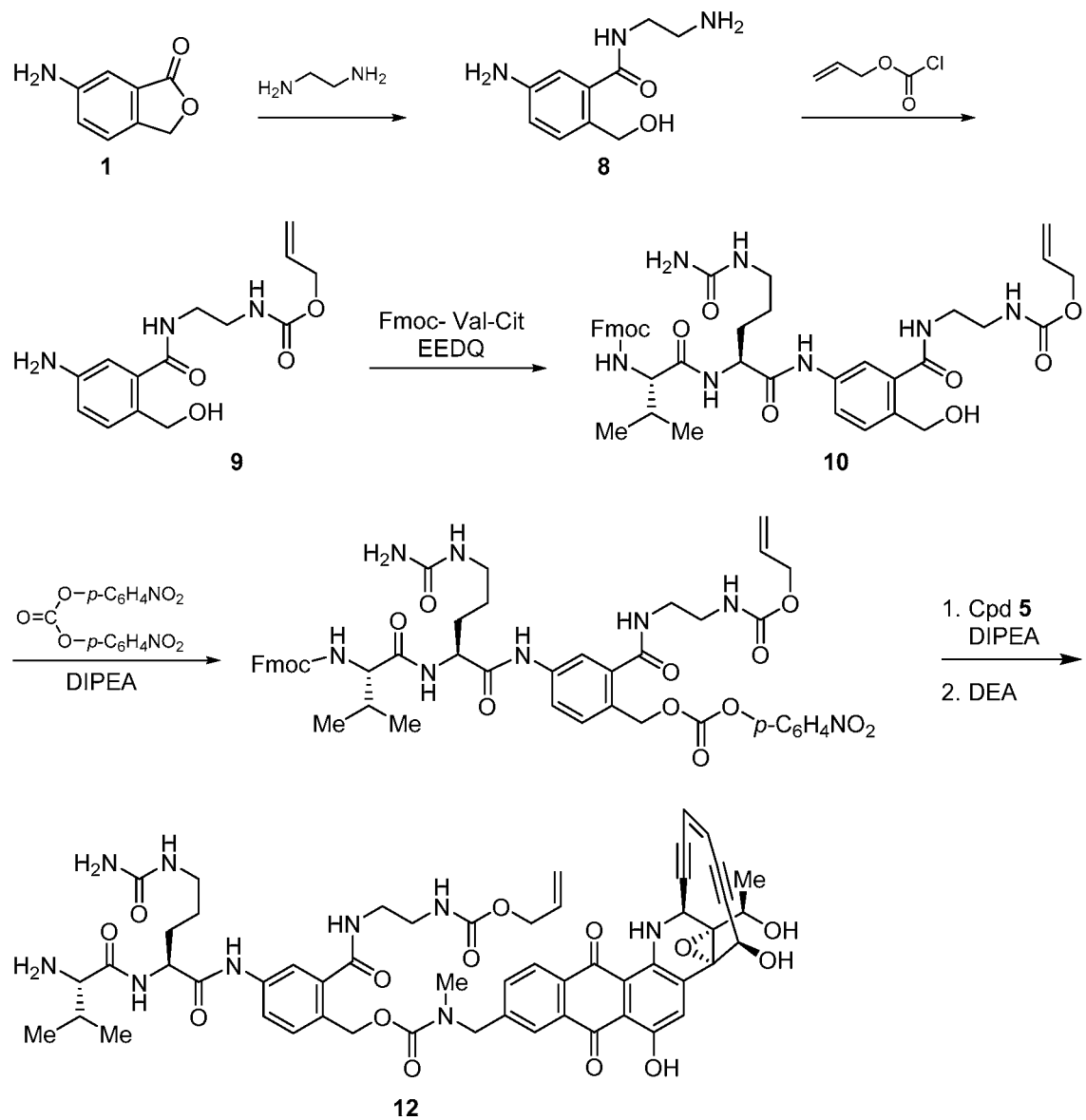
Figure 3B:
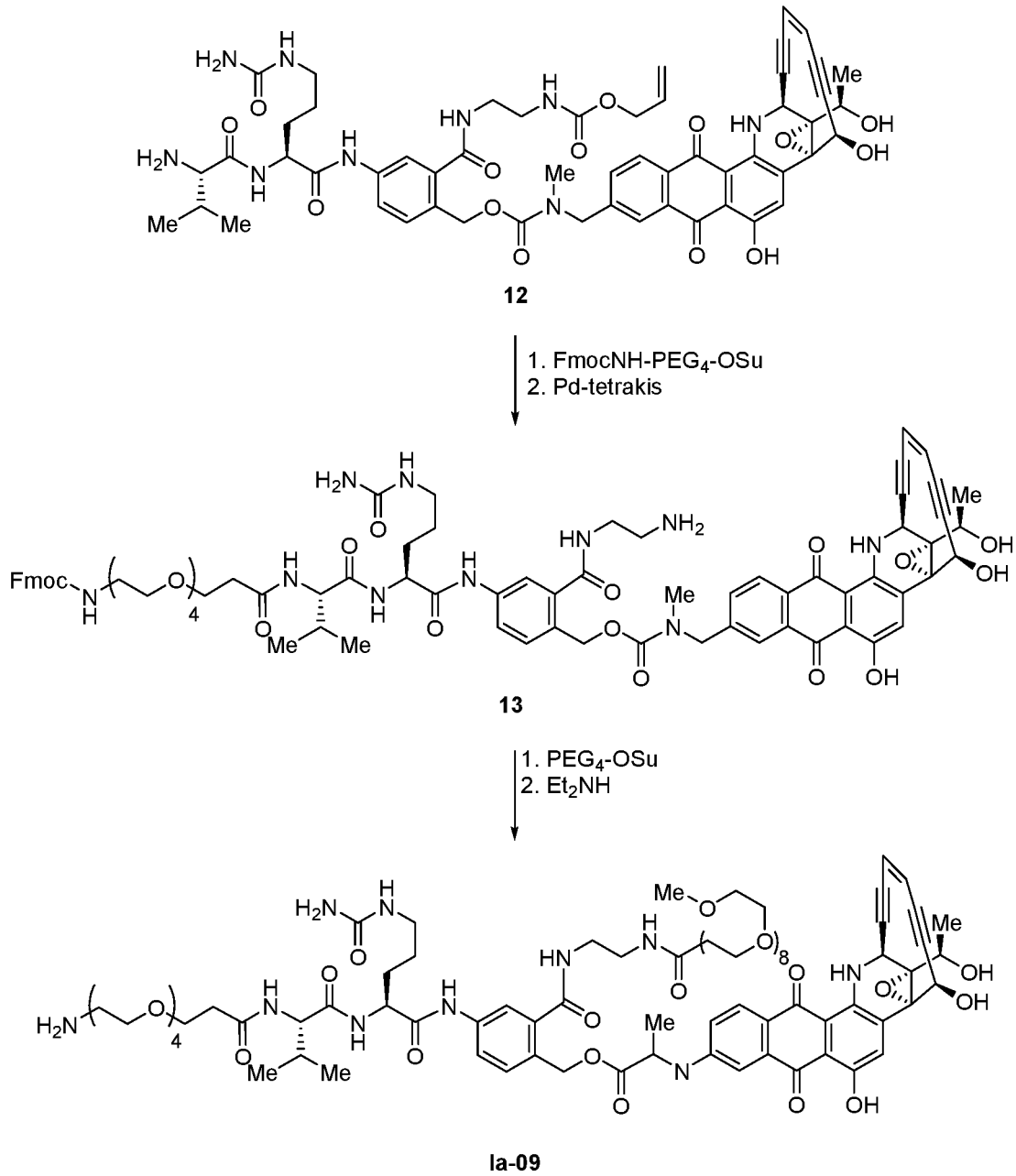
Figure 3C:
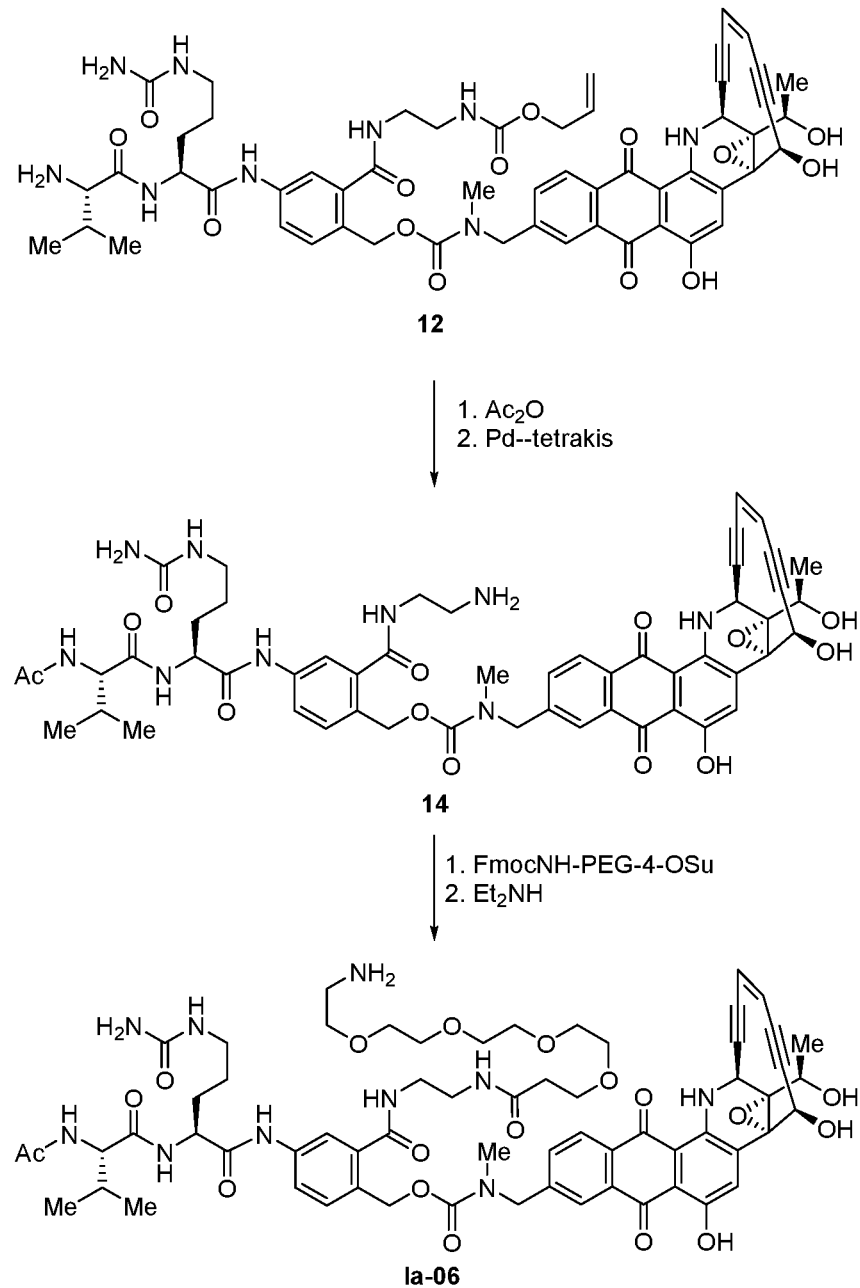

FIGS. 3A, 3B, and 3C show, in combination, a Scheme B for the synthesis of compounds disclosed herein.

Figure 4:
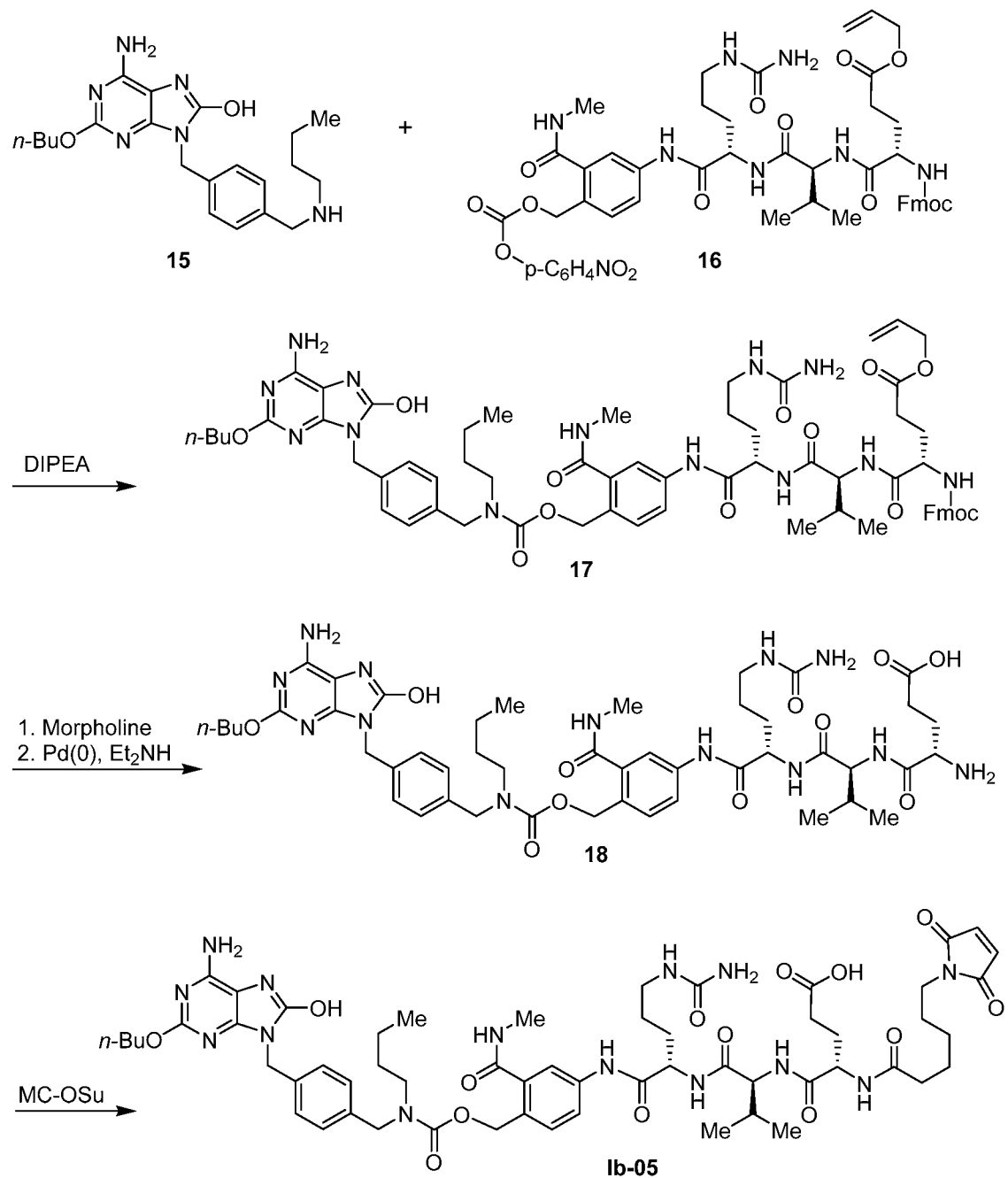

FIG. 4 shows a Scheme C for the synthesis of compounds disclosed herein.

Figure 5:
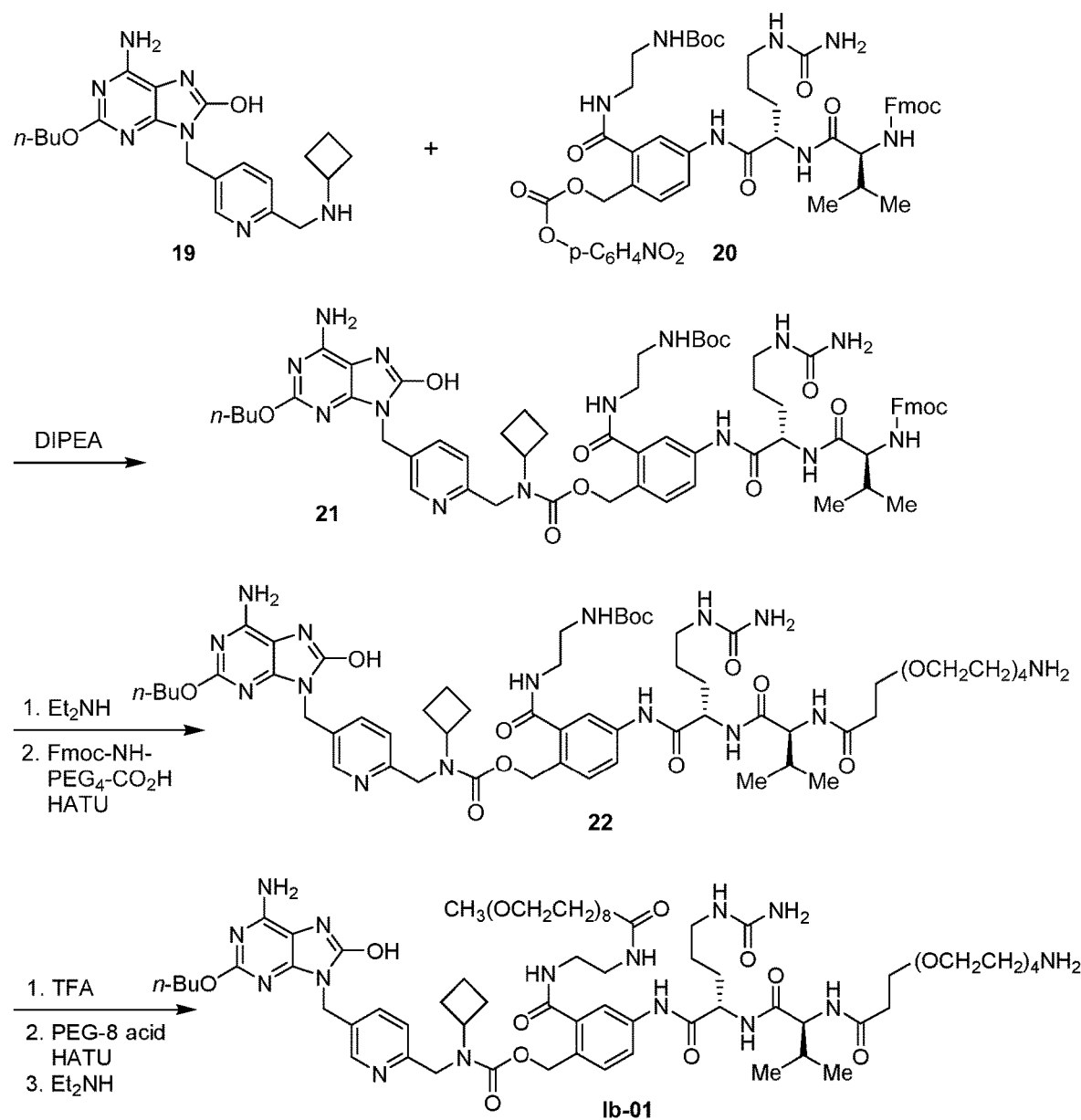

FIG. 5 shows a Scheme D for the synthesis of compounds disclosed herein.

DETAILED DESCRIPTION OF THE INVENTION

Definitions

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (C1q) of the classical complement system. An antibody is said to "specifically bind" to an antigen X if the antibody binds to antigen X with a $K_D$ of $5 \times 10^{-8}$ M or less, more preferably $1 \times 10^{-8}$ M or less, more preferably $6 \times 10^{-9}$ M or less, more preferably $3 \times 10^{-9}$ M or less, even more preferably $2 \times 10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

Unless indicated otherwise—for example by reference to the linear numbering in a SEQ ID NO: listing—references to the numbering of amino acid positions in an antibody heavy or light chain variable region ($V_H$ or $V_L$) are according to the Kabat system (Kabat et al., "Sequences of proteins of immunological interest, 5th ed., Pub. No. 91-3242, U.S. Dept. Health & Human Services, NIH, Bethesda, Md., 1991, hereinafter "Kabat") and references to the numbering of amino acid positions in an antibody heavy or light chain constant region ($C_{H1}$, $C_{H2}$, $C_{H3}$, or $C_L$) are according to the EU index as set forth in Kabat. See Lazar et al., US 2008/0248028 A1, the disclosure of which is incorporated herein by reference, for examples of such usage. Further, the ImMunoGeneTics Information System (IMGT) provides at its website a table entitled "IMGT Scientific Chart: Correspondence between C Numberings" showing the correspondence between its numbering system, EU numbering, and Kabat numbering for the heavy chain constant region.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_{1-5}$ aliphatic," "$C_1$-$C_5$ aliphatic," or "$C_1$ to $C_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_{2-4}$ alkene, $C_4$-$C_7$ cycloaliphatic, etc. In a similar vein, a term such as "$(CH_2)_{1-3}$" is to be understand as shorthand for the subscript being 1, 2, or 3, so that such term represents $CH_2$, $CH_2CH_2$, and $CH_2CH_2CH_2$.

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Preferred heterocycloaliphatic moieties consist of one ring, 5- to 6-membered in size. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine, unless a narrower meaning is indicated.

"Aryl" means a hydrocarbon moiety having a mono-, bi-, or tricyclic ring system (preferably monocyclic) wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system (preferably 5- to 7-membered monocyclic) wherein each ring has from 3 to 7 carbon atoms and at least one ring is an aromatic ring containing from 1 to 4 heteroatoms independently selected from from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of a heteroaryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein. Where a moiety is identified as being "unsubstituted or substituted" or "optionally substituted," in a preferred embodiment such moiety is unsubstituted.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, C$_1$-C$_4$alkyoxy, O(C$_2$-C$_4$ alkylene)OH, and O(C$_2$-C$_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are C$_1$-C$_4$ alkyl, cyano, nitro, halo, and C$_1$-C$_4$alkoxy.

Where a range is stated, as in "C$_1$-C$_5$ alkyl" or "5 to 10%," such range includes the end points of the range, as in C$_1$ and C$_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include C$_1$-C$_5$ alkyl, C$_2$-C$_5$ alkenyl or C$_2$-C$_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

In the formulae of this specification, a wavy line ( ~~~ ) transverse to a bond or an asterisk (*) at the end of the bond denotes a covalent attachment site. For instance, a statement that R is

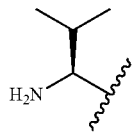

or that R is

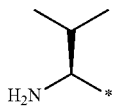

in the formula

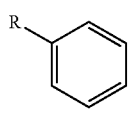

means

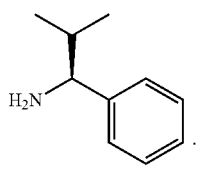

In the formulae of this specification, a bond traversing an aromatic or heteroaromatic ring between two carbons thereof means that the group attached to the bond may be located at any of the positions of the aromatic or heteroaromatic ring made available by removal of a hydrogen that is implicitly there. By way of illustration, the formula

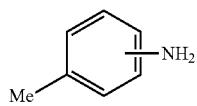

represents

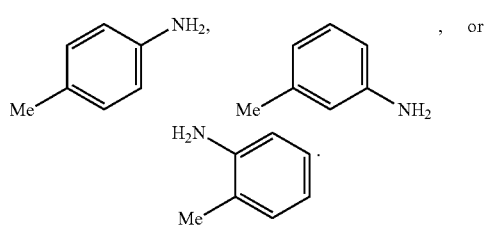

In other illustrations,

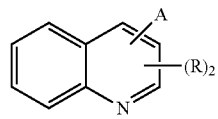

represents

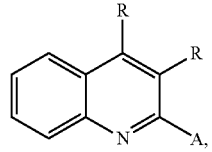 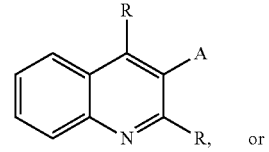

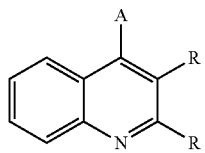 and 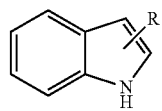

represents

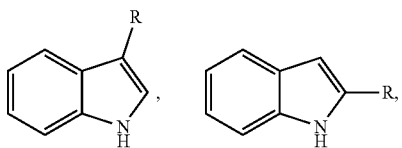

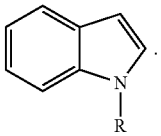

Generally, tautomeric structures have been rendered herein in the enol form, as a matter of consistency and convenience.

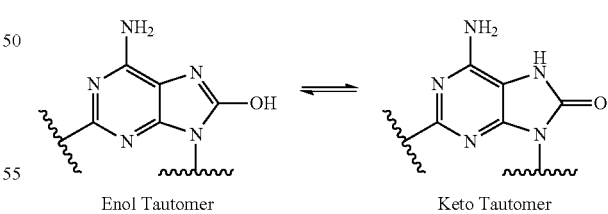

Enol Tautomer          Keto Tautomer

Those skilled in the art will appreciate that they could also have be rendered in the equivalent keto form and that the two tautomers equivalent.

Compounds

We have discovered that placing a substituent $R^4$ at a position ortho to the benzyloxycarbonyl group in a PABC moiety substantially inhibits cleavage of the bond between peptide

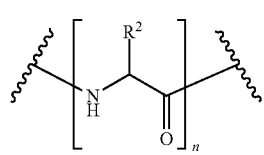

and the substituted PABC group

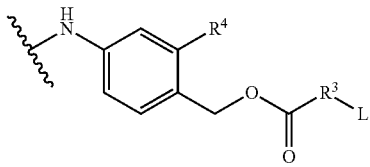

in mouse serum but yet does not substantially inhibit cleavage of the same bond by cathepsin B, as evidenced by the data presented below. Consequently, the compounds disclosed herein can be conjugated to antibodies that are amenable to evaluation in mouse models.

By substantially inhibiting cleavage of the aforementioned bond by mouse serum, we mean that there is 10% or less cleavage, preferably 6% or less cleavage after 24 h under the conditions described in the EXAMPLES section below. Conversely, by not substantially inhibiting cleavage of the aforementioned bond by cathepsin B, we mean that there is 90% or more cleavage after 24 h under the conditions described in the EXAMPLES section below.

In formulae (I), preferably $R^1$ is H, $CH_3$, $NH_2$, $N_3$,

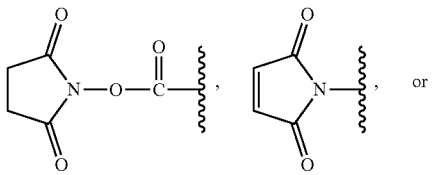

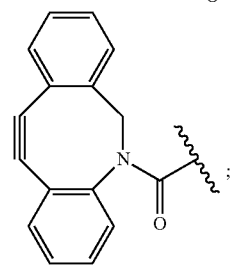

with especially preferred ones being $NH_2$ and

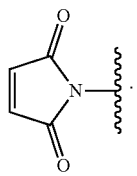

In formulae (I) and (II), preferably $R^3$ is NH,

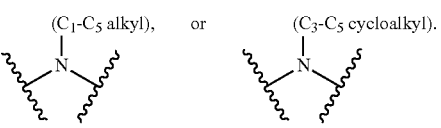

Especially preferred $R^3$ are NH,

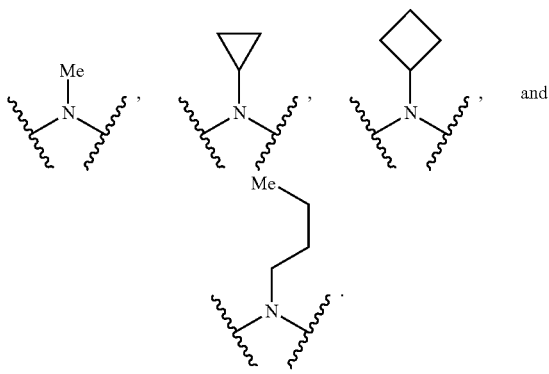

In formulae (I) and (II), $R^4$ preferably is

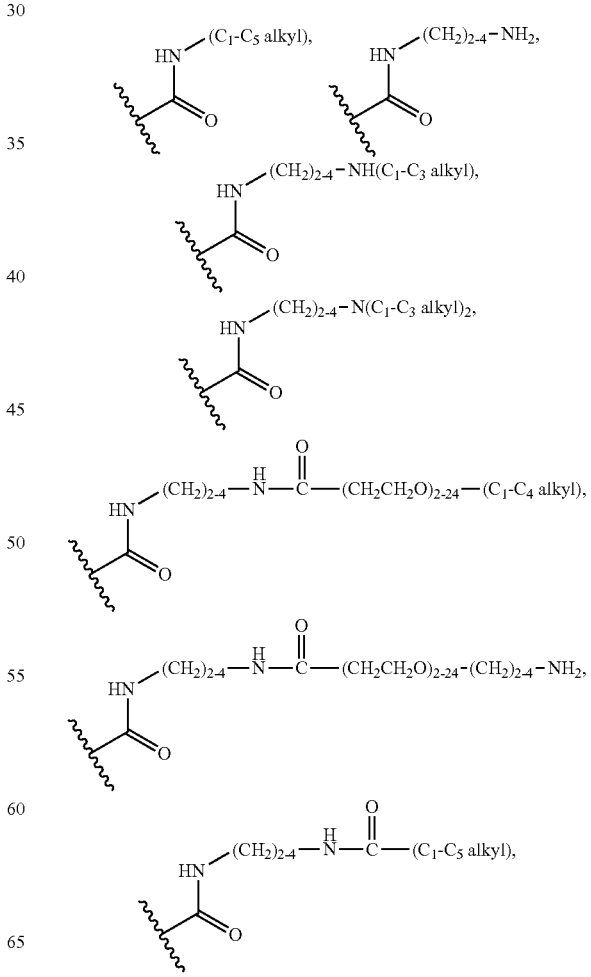

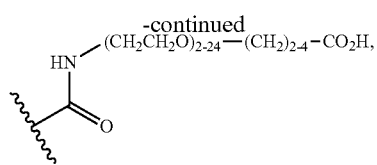

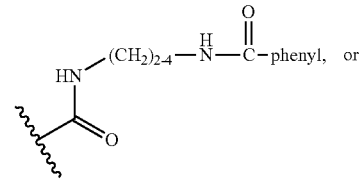

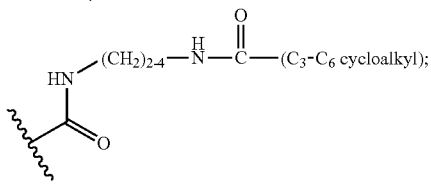

a phenyl or $C_3$-$C_6$ cycloalkyl group being optionally substituted with F, Cl, CN, $NO_2$, or $C_1$-$C_3$ alkyl.

$R^4$ more preferably is

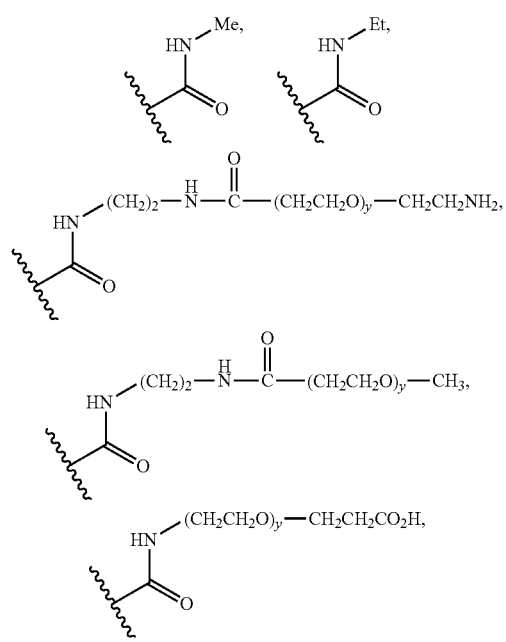

where y is 4, 8, 12, or 24.

Preferably, in formulae (I) and (II), $R^2$ is the side chain residue of an amino acid selected from valine (Val), glutamic acid (Glu), citrulline (Cit), lysine (Lys), alanine (Ala), phenylalanine (Phe), arginine (Arg), and glycine (Gly).

Preferably, in formulae (I) and (II), the peptide group

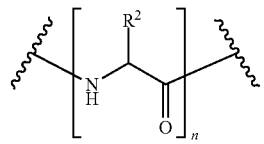

is one that is cleavable by cathepsin B but is stable in human serum. Examples of such peptide groups include (recited in the N-to-C direction): Val-Cit, Glu-Val-Cit, Phe-Lys, Phe-Arg, Val-Lys, Ala-Lys, Phe-Phe-Lys, Gly-Phe-Lys, Val-Ala, Ala-Val-Cit, and Val-Gly.

As the peptide

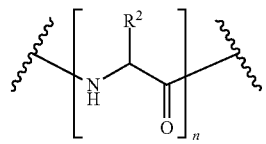

is oriented in the N-to-C (amino-to-carboxyl) direction, spacer group X connects the N-terminus of the peptide to $R^1$. Typically, X comprises a carbonyl group forming an amide bond with the N-terminus of the peptide, but X can be connected instead to a functional group on the side chain of the terminal amino acid, such as a Glu or Asp carboxyl group. Where $R^1$ is alkyl, X can be simply carbonyl (C=O). Other embodiments of X are:

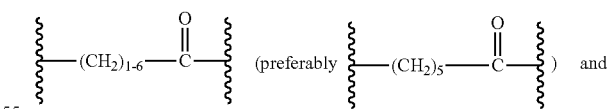

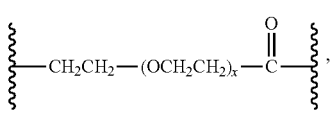

where x is an integer from 2 to 24, inclusive, preferably 2, 4, or 8.

In one embodiment, compounds of formula (I) are represented by formula (Ia):

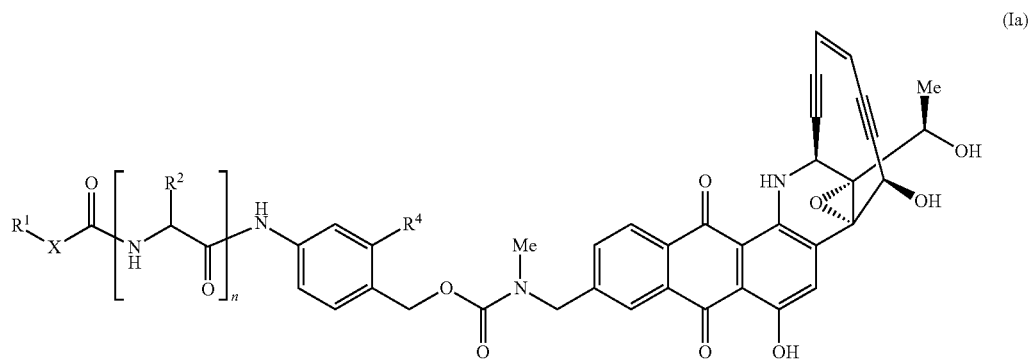

(The above-stated preferences for $R^1$, X, $R^2$, and $R^4$ in the context of formula (I) also apply to formula (Ia).)

In formula (Ia) the bioactive molecule corresponding to L-$R^3$H is 8-aminomethyluncialamycin (Nicolaou et al., U.S. Pat. No. 9,777,013 B2 (2017)), a synthetic analogue of the natural product uncialamycin (Davies et al., *Org. Lett.* 2005, 7 (23), 5233), which is a cytotoxin that has antitumor properties.

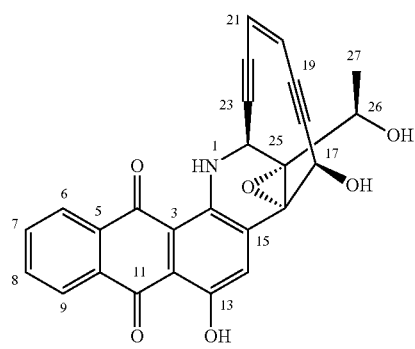

Uncialamycin

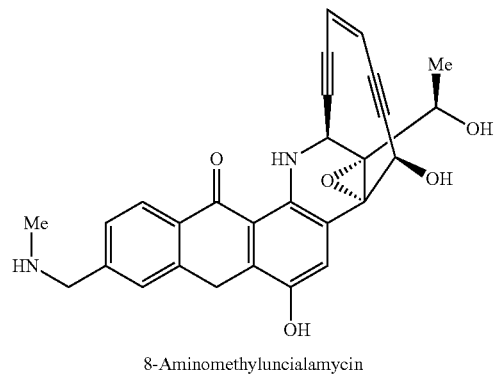

8-Aminomethyluncialamycin

Examples of compounds according to formula (Ia) are shown in Table A.

TABLE A

Compounds According to Formula (Ia)

| Compound | 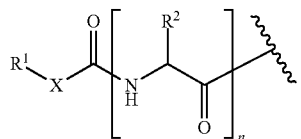 |  |
|---|---|---|
| (Ia-01) | 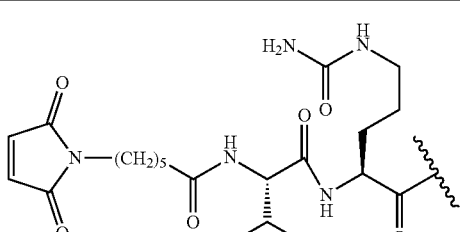 | 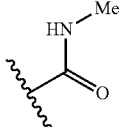 [SMILES: *C(=O)NC] |

TABLE A-continued

Compounds According to Formula (Ia)

| Compound | | |
|---|---|---|
| (Ia-02) (x = 8) (Ia-03) (x = 4) (Ia-04) (x = 2) | [structure: H₂N-CH₂CH₂-[O-CH₂CH₂]ₓ-C(=O)-NH-CH(CO₂H)-C(=O)-NH-CH(CH(Me)Me)-C(=O)-NH-CH(CH₂CH₂CH₂NHC(=O)NH₂)-C(=O)-] | [structure: -C(=O)-NH-Me] |
| (Ia-05) | [structure: H₂N-CH₂CH₂-[O-CH₂CH₂]₄-C(=O)-NH-CH(CH(Me)Me)-C(=O)-NH-CH(CH₂CH₂CH₂NHC(=O)NH₂)-C(=O)-] | [structure: -C(=O)-NH-CH₂CH₂-NH₂] |
| (Ia-06) | [structure: Me-C(=O)-NH-CH(CH(Me)Me)-C(=O)-NH-CH(CH₂CH₂CH₂NHC(=O)NH₂)-C(=O)-] | [structure: -C(=O)-NH-CH₂CH₂-NH-C(=O)-[CH₂CH₂-O]₄-CH₂CH₂-NH₂] |
| (Ia-07) | [structure: H₂N-CH₂CH₂-[O-CH₂CH₂]₄-C(=O)-NH-CH(CH(Me)Me)-C(=O)-NH-CH(CH₂CH₂CH₂NHC(=O)NH₂)-C(=O)-] | [structure: -C(=O)-NH-CH₂CH₂-NH-C(=O)-Me] |

TABLE A-continued
Compounds According to Formula (Ia)
| Compound | | |
|---|---|---|
| (Ia-08) | | |
| (Ia-09) (y = 8)<br>(Ia-10) (y = 12)<br>(Ia-11) (y = 24) | | |
In another embodiment, compounds according to formula (I) are represented by formulae (Ib):
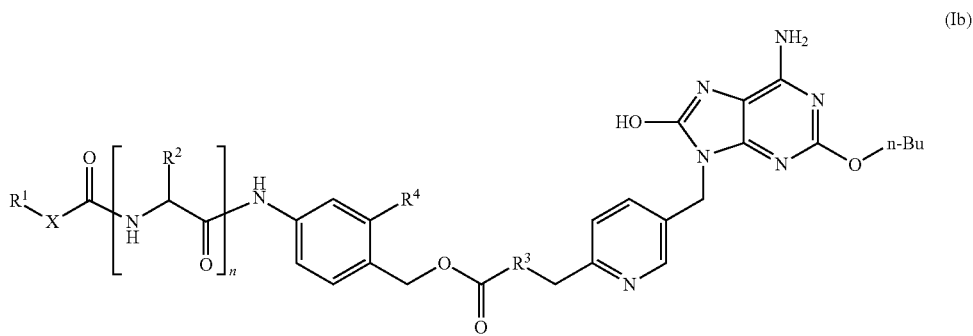

(The above-stated preferences for $R^1$, X, $R^2$, $R^3$, and $R^4$ in the context of formula (I) also apply to formula (Ib).)

In formula (Ib), the biologically active molecule corresponding to L-$R^3$H is

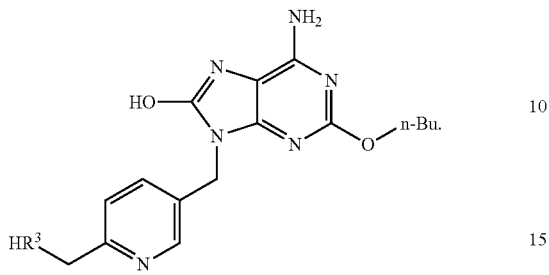

Molecules of this type are agonists of Toll-like receptor 7 (TLR7). The activation of TLR7 by them can have an adjuvant effect on vaccines and immunotherapy agents.

Examples of compounds according to formula (Ib) are shown in Table B.

TABLE B

Compounds According to Formula (Ib)

Table C shows how compounds having a substituent ortho to the benzyloxycarbonyl group in the PABC group as disclosed herein are stable in both human and mouse serum (or have improved stability in mouse serum) but yet cleavable by cathepsin B. In contrast, two controls with an unsubstituted PABC group, one with an 8-aminomethyluncialamycin payload (Compound A) and one with a TLR7 agonist payload (Compound B), were both unstable in mouse serum.

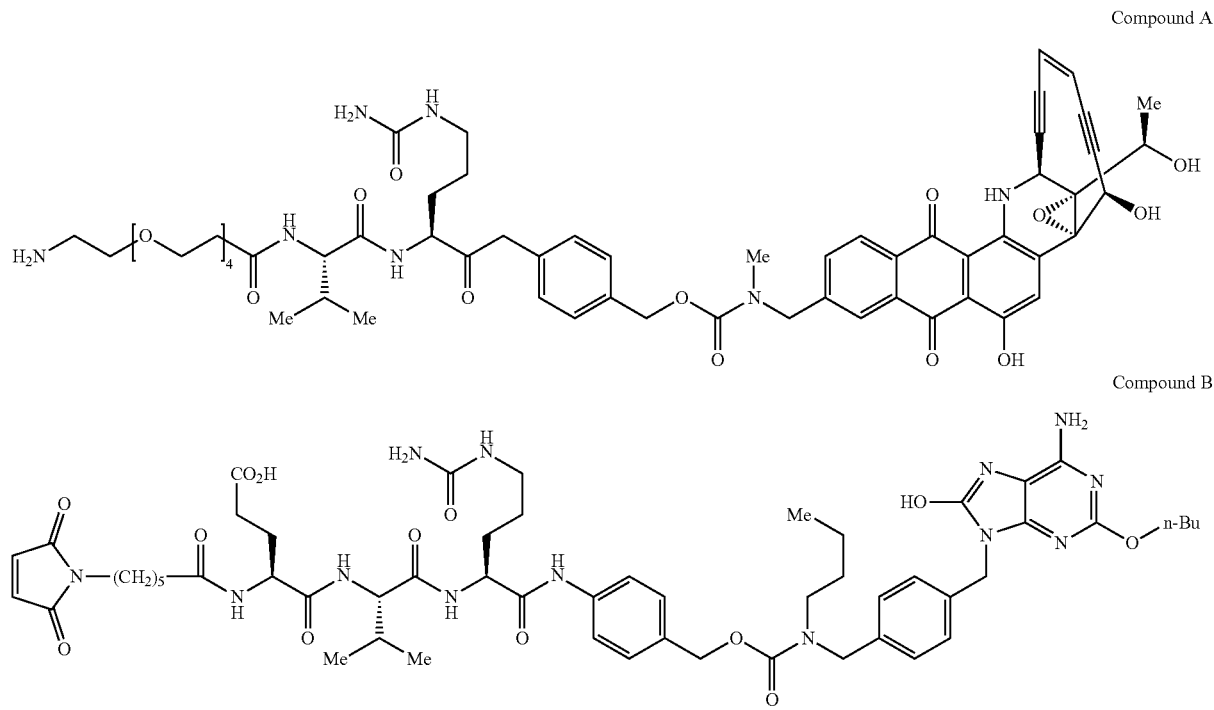

TABLE C

Stability of Compounds in Human and Mouse Serum and Cleavage by Cathepsin B

| Compound | Stability in Human Serum (% cleaved after 24 hours) | Stability in Mouse Serum (% cleaved after 24 hours) | Cathepsin B Cleavage (% cleaved after 24 hours) |
|---|---|---|---|
| Compound A | 0 | 100 | 100 |
| Compound B | 0 | 50 | 100 |
| (Ia-01) | 0 | 50 | 100 |
| (Ia-03) | 0 | 7 | 100 |
| (Ia-05) | 0 | 3 | 100 |
| (Ia-06) | 0 | 6 | 100 |
| (Ib-01) | 0 | 3 | 100 |
| (Ib-05) | 0 | 2 | 100 |

Conjugates

Conjugates of formula (II) can be prepared from an antibody and a compound of formula (I) in numerous ways, according to the identity of the group $R^1$.

Where $R^1$ is an OH group, it can be esterified with a carboxy group on the antibody, for example, on an aspartic or glutamic acid side chain or at the C-terminus of a heavy or light chain of the antibody.

Where $R^1$ is a $CO_2H$ group, it can be esterified with an OH group on the antibody, such as in the side chain of a serine residue, or amidated with an amino group on the antibody, such as a lysine side chain.

Where $R^1$ is an N-hydroxysuccinimide ester

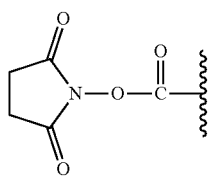 [SMILES: *C(=O)ON1C(=O)CCC1=O]

it is functionally an activated carboxyl group and can be amidated by reaction with an amino group (e.g., from lysine) in the antibody.

In one preferred embodiment, $R^1$ is a maleimide group

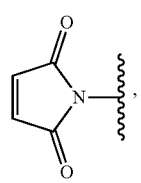 [SMILES: *N1C(=O)C=CC1=O]

which can be conjugated with an SH group on the antibody (e.g., from cysteine or from the chemical modification of the antibody to introduce a sulfhydryl functionality), in a Michael addition reaction.

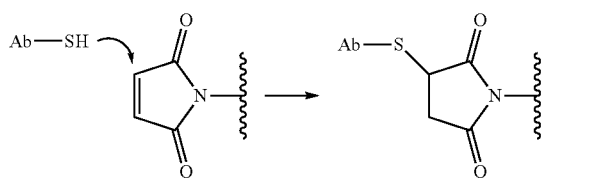

Where an antibody does not have a cysteine SH available for conjugation (most antibody cysteine SH's are tied up in disulfide bonds), an 8-amino group in the side chain of a lysine residue can be reacted with 2-iminothiolane or N-succinimidyl-3-(2-pyridyldithio)-propionate ("SPDP") to introduce a free thiol (—SH) group—creating a cysteine surrogate, as it were, which can then be used for conjugation.

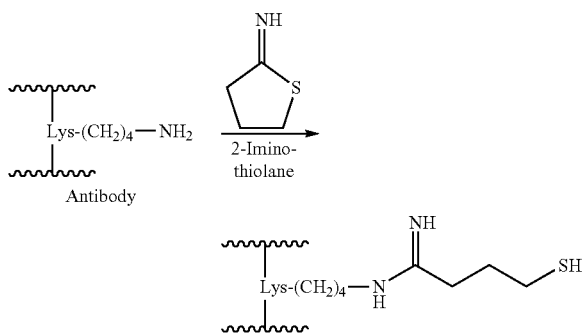

Typically, a thiolation level of two to three thiols per antibody is achieved. For a representative procedure, see Cong et al., U.S. Pat. No. 8,980,824 B2 (2015), the disclosure of which is incorporated herein by reference.

In a reversed arrangement, an antibody can be modified with N-succinimidyl 4-(maleimidomethyl)-cyclohexanecarboxylate ("SMCC") or its sulfonated variant sulfo-SMCC, both of which are commercially available, to introduce a maleimide group thereto. Then, conjugation can be effected with compound of formula (I) where $R^1$ is SH.

An alternative conjugation method employs copper-free "click chemistry," in which an azide group adds across a strained cyclooctyne to form an 1,2,3-triazole ring. See, e.g., Agard et al., J. Amer. Chem. Soc. 2004, 126, 15046; Best, Biochemistry 2009, 48, 6571, the disclosures of which are incorporated herein by reference. The azide can be located on the antibody and the cyclooctyne on a compound of formula (I), or vice-versa. A preferred cyclooctyne group is dibenzocyclooctyne (DIBO). Various reagents having a DIBO group are available from Invitrogen/Molecular Probes, Eugene, Oregon. The reaction below illustrates click chemistry conjugation for the instance in which the DIBO group is attached to the antibody (Ab):

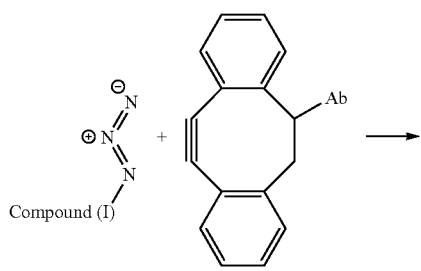

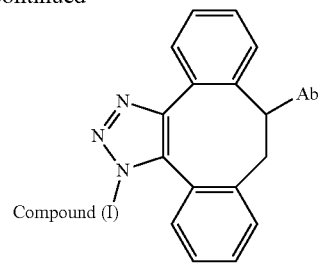

Yet another conjugation technique involves introducing a non-natural amino acid into an antibody, with the non-natural amino acid providing a functionality for conjugation with a reactive functional group in the drug moiety. For instance, the non-natural amino acid p-acetylphenylalanine can be incorporated into an antibody or other polypeptide, as taught in Tian et al., WO 2008/030612 A2 (2008). The ketone group in p-acetylphenyalanine can be a conjugation site via the formation of an oxime with a hydroxylamino group on the linker-drug moiety. Alternatively, the non-natural amino acid p-azidophenylalanine can be incorporated into an antibody to provide an azide functional group for conjugation via click chemistry, as discussed above. Non-natural amino acids can also be incorporated into an antibody or other polypeptide using cell-free methods, as taught in Goerke et al., US 2010/0093024 A1 (2010) and Goerke et al., Biotechnol. Bioeng. 2009, 102 (2), 400-416.

In a preferred embodiment, $R^1$ is $NH_2$, allowing conjugation using the enzyme transglutaminase.

Transglutaminase (preferably bacterial transglutaminase from Streptomyces mobaraensis or BTG) forms an amide bond between the side chain carboxamide of a glutamine (the amine acceptor) and an alkyleneamino group (the amine donor), which can be, for example, the ε-amino group of a lysine or a 5-amino-n-pentyl group (Jeger et al., Angew. Chem. Int. Ed. 2010, 49, 9995). The alkyleneamino group can be on a compound of formula (I), with $R^1$ being $NH_2$.

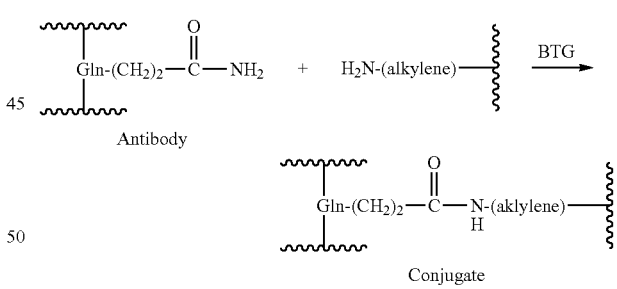

The positioning of a glutamine residue on a polypeptide chain has a large effect on its susceptibility to BTG mediated transamidation. None of the glutamine residues on an antibody are normally BTG substrates. However, if the antibody is deglycosylated—the glycosylation site being asparagine 297 (N297; numbering per EU index as set forth in Kabat et al., "Sequences of proteins of immunological interest," 5th ed., Pub. No. 91-3242, U.S. Dept. Health & Human Services, NIH, Bethesda, Md., 1991; hereinafter "Kabat") of the heavy chain—nearby glutamine 295 (Q295) is rendered BTG susceptible. An antibody can be deglycosylated enzymatically by treatment with PNGase F (Peptide-N-Glycosidase F). Alternatively, an antibody can be synthesized glycoside free by introducing an N297A mutation in the constant region, to eliminate the N297 glycosylation site. Further, it has been shown that an N297Q substitution not only eliminates glycosylation, but also introduces a second glutamine residue (at position 297) that too is an amine acceptor. Thus, in one embodiment, the antibody is deglycosylated. In another embodiment, the antibody has an N297Q substitution. Those skilled in the art will appreciate that deglycosylation by post-synthesis modification or by introducing an N297A mutation generates two BTG-reactive glutamine residues per antibody (one per heavy chain, at position 295), while an antibody with an N297Q substitution will have four BTG-reactive glutamine residues (two per heavy chain, at positions 295 and 297).

An antibody can also be rendered susceptible to BTG-mediated conjugation by introducing into it a glutamine containing peptide, or "tag," as taught, for example, in Pons et al., US 2013/0230543 A1 (2013) and Rao-Naik et al., WO 2016/144608 A1.

In a complementary approach, the substrate specificity of BTG can be altered by varying its amino acid sequence, such that it becomes capable of reacting with glutamine 295 in an unmodified antibody, as taught in Rao-Naik et al., WO 2017/059158 A1 (2017).

While the most commonly available bacterial transglutaminase is that from *S. mobaraensis*, transglutaminase from other bacteria, having somewhat different substrate specificities, can be considered, such as transglutaminase from *Streptoverticillium ladakanum* (Hu et al., US 2009/0318349 A1 (2009), US 2010/0099610 A1 (2010), and US 2010/0087371 A1 (2010)).

Preferably, in a conjugate of formula (II), $R^5$ is

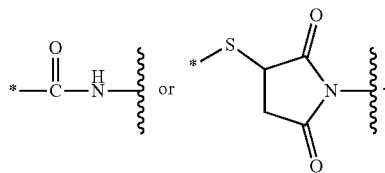

Many different antibodies can be conjugated to a compound of formula (I). Preferably the antibody is an antibody against a tumor associated antigen, allowing the selective targeting of cancer cells. Examples of such antigens include: mesothelin, prostate specific membrane antigen (PSMA), CD19, CD22, CD30, CD70, B7H3, B7H4 (also known as 08E), protein tyrosine kinase 7 (PTK7), glypican-3, RG1, fucosyl-GM1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., U.S. Pat. No. 8,609,816 B2 (2013; B7H4, also known as 08E; in particular antibodies 2A7, 1G11, and 2F9); Rao-Naik et al., U.S. Pat. No. 8,097,703 B2 (2012; CD19; in particular antibodies 5G7, 13F1, 46E8, 21D4, 21D4a, 47G4, 27F3, and 3C10); King et al., U.S. Pat. No. 8,481,683 B2 (2013; CD22; in particular antibodies 12C5, 19A3, 16F7, and 23C6); Keler et al., U.S. Pat. No. 7,387,776 B2 (2008; CD30; in particular antibodies 5F11, 2H9, and 17G1); Terrett et al., U.S. Pat. No. 8,124,738 B2 (2012; CD70; in particular antibodies 2H5, 10B4, 8B5, 18E7, and 69A7); Korman et al., U.S. Pat. No. 6,984,720 B1 (2006; CTLA-4; in particular antibodies 10D1, 4B6, and 1E2); Vistica et al., U.S. Pat. No. 8,383,118 B2 (2013, fucosyl-GM1, in particular antibodies 5B1, 5B1a, 7D4, 7E4, 13B8, and 18D5); Korman et al., U.S. Pat. No. 8,008,449 B2 (2011; PD-1; in particular antibodies 17D8, 2D3, 4H1, 5C4, 4A11, 7D3, and 5F4); Huang et al., US 2009/0297438 A1 (2009; PSMA. in particular antibodies 1C3, 2A10, 2F5, 2C6); Cardarelli et al., U.S. Pat. No. 7,875,278 B2 (2011; PSMA; in particular antibodies 4A3, 7F12, 8C12, 8A11, 16F9, 2A10, 2C6, 2F5, and 1C3); Terrett et al., U.S. Pat. No. 8,222,375 B2 (2012; PTK7; in particular antibodies 3G8, 4D5, 12C6, 12C6a, and 7C8); Terrett et al., U.S. Pat. No. 8,680,247 B2 (2014; glypican-3; in particular antibodies 4A6, 11E7, and 16D10); Harkins et al., U.S. Pat. No. 7,335,748 B2 (2008; RG1; in particular antibodies A, B, C, and D); Terrett et al., U.S. Pat. No. 8,268,970 B2 (2012; mesothelin; in particular antibodies 3C10, 6A4, and 7B1); Xu et al., US 2010/0092484 A1 (2010; CD44; in particular antibodies 14G9.B8.B4, 2D1.A3.D12, and 1A9.A6.B9); Deshpande et al., U.S. Pat. No. 8,258,266 B2 (2012; IP10; in particular antibodies 1D4, 1E1, 2G1, 3C4, 6A5, 6A8, 7C10, 8F6, 10A12, 10A12S, and 13C4); Kuhne et al., U.S. Pat. No. 8,450,464 B2 (2013; CXCR4; in particular antibodies F7, F9, D1, and E2); and Korman et al., U.S. Pat. No. 7,943,743 B2 (2011; PD-Li; in particular antibodies 3G10, 12A4, 10A5, 5F8, 10H10, 1B12, 7H1, 11E6, 12B7, and 13G4); the disclosures of which are incorporated herein by reference.

EXAMPLES

The practice of this invention can be further understood by reference to the following examples, which are provided by way of illustration and not of limitation.

A table after the Examples lists acronyms and abbreviations used herein and their meanings.

Example 1—Blood Serum Stability

The following procedure was used for testing the blood serum stability of linkers in mouse, rat, or human serum 5 µL of text compound (0.5 mM in DMSO) was transferred separately to individual tubes containing 120 µl of 1× phosphate buffered saline, mouse, rat or human serum. The samples were incubated at 37° C. for 0, 1, 2, 4, and 24 hours. After each of the time points, an aliquot of 20 µl was taken from the samples and quenched with 60 µl of 75:25:0.1 MeOH:acetonitrile:formic acid. After quenching, all samples were held at −20° C. for 1 hour and further centrifuged at 14000 rpm for 15 mins. The supernatant was transferred to a fresh vial and stored at −20° C. until analysis.

Samples were analyzed using LC-MS/MS on Agilent 6530 Q-TOF mass spectrometer connected to an Agilent 1290 UPLC. 3 µL of samples were injected onto a Waters BEH C18 Column (2.1×50 mm, 1.7 µm) maintained at 60° C. The compounds were eluted from column at a flow rate of 0.4 mL/min, using a gradient of 0.1% formic acid in water and 0.1% formic acid in acetonitrile. The total run time is 9.5 min.

Example 2—Cathepsin B Cleavage

The following procedure was used for testing the cathepsin B cleavage of linkers.

7.5 µL of test compound (0.5 mM in DMSO) was transferred to individual tube containing 135 µl of Cathepsin B buffer (25 mM Sodium Acetate, 1 mM EDTA, 1 mM DTT, pH 5.5) and the digestion was started by the addition of 7.5 µl of the diluted Cathepsin B enzyme (Activated, 1.45 µM, 0.1 units). The samples were incubated at 37° C. for 24 h. After 24 h, a 20 μL aliquot was taken and quenched with 80 μL of 75:25:0.1 MeOH:acetonitrile:formic acid. Negative control was also included, without the addition of Cathepsin B. A control compound (structure below) was digested similarly and included as positive control. After quenching, all samples were held at −20° C. for 1 h and further centrifuged at 14,000 rpm for 5 min. The supernatant was transferred to a fresh tube and put in an UPLC autosampler for analysis, per the procedure of the preceding example.

Positive control compound

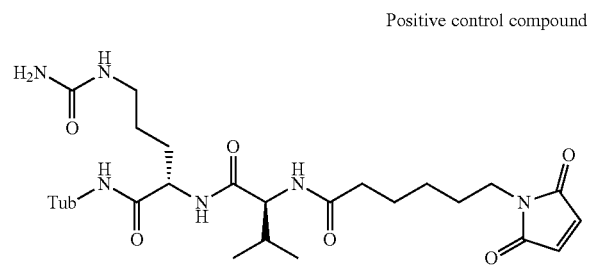

In the above structure, "Tub" denotes a tubulysin analog (Cheng et al., U.S. Pat. No. 8,394,922 B2 (2013). The valine-citrulline (Val-Cit) dipeptide is a known substrate for cathepsin B.

Example 3—Preparation of Conjugates Using Transglutaminase

The following procedure can be used for transglutaminase mediated conjugation of linker compounds wherein the linker has an amine group that can act as an amine donor (e.g., compounds Ia-02 through Ia-12 and Ib-01 through Ib-04). The antibody can be one that has a transglutaminase-reactive glutamine, for example one with an N297A or N297Q substitution. Conjugation is carried out by recombinant bacterial transglutaminase with a molar ratio of antibody:enzyme of 5:1. The conjugation is carried out using standard protocols in 50 mM Tris buffer, pH 8.0, incubated overnight at 37° C. The resulting conjugate is purified on a Protein A column, pre-equilibrated with 50 mM Tris, pH 8.0. The conjugate is eluted with 0.1 M sodium citrate buffer, pH 3.5. The eluted fractions are neutralized with 1M Tris pH 9.0. The conjugate can be formulated in 20 mg/mL Sorbitol, 10 mg/mL Glycine, pH 5.0.

Figure 1:
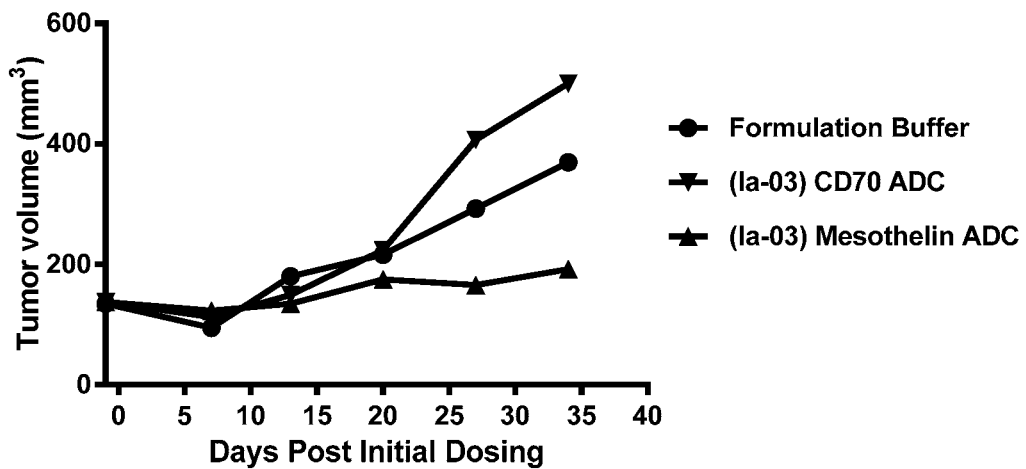
FIG. 1 shows the efficacy of an ADC made with a compound of this invention against mesothelioma in an animal model.
Figure 2A:
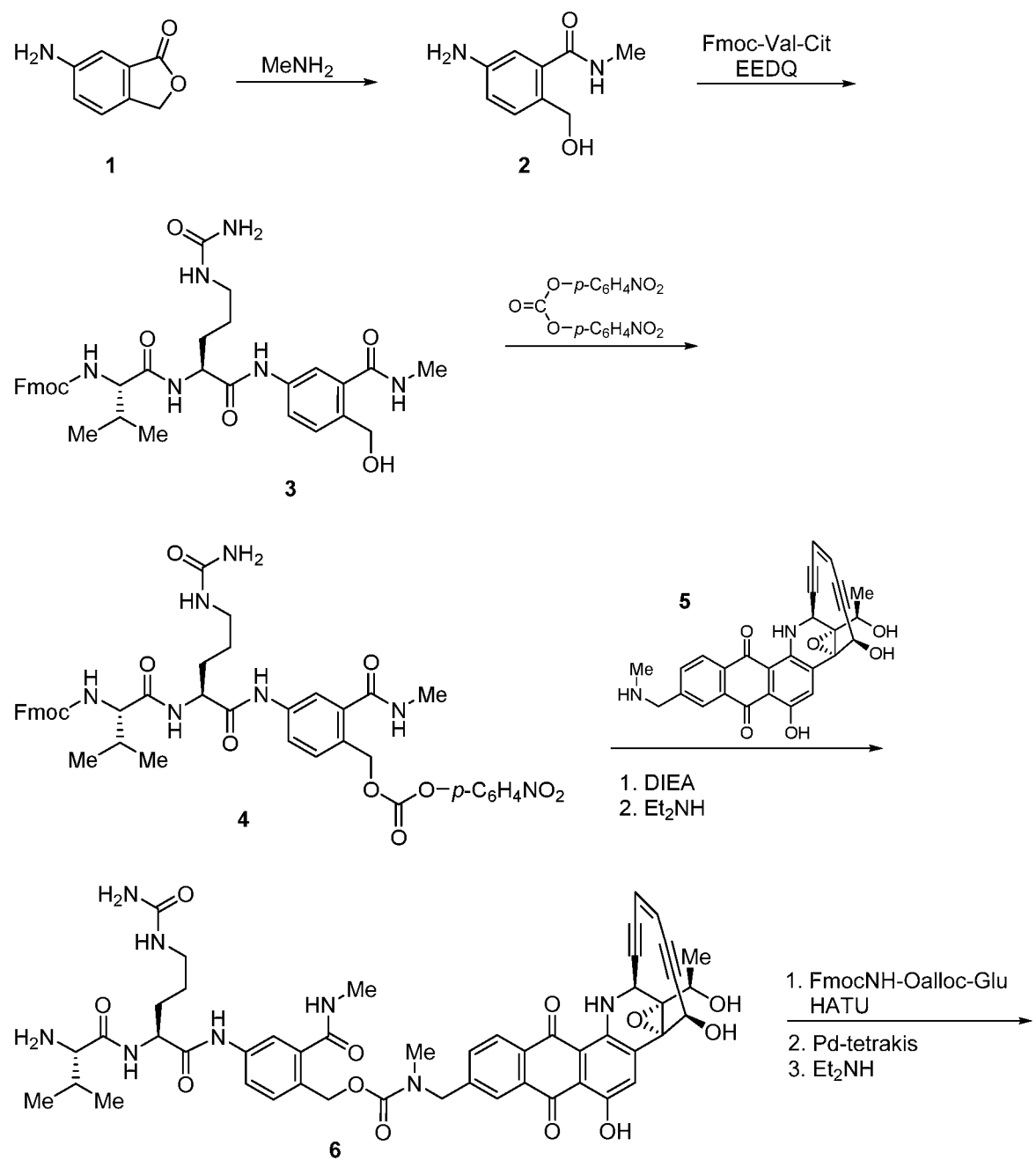
FIGS. 2A and 2B show, in combination, a Scheme A for the synthesis of compounds disclosed herein.
Figure 2B:
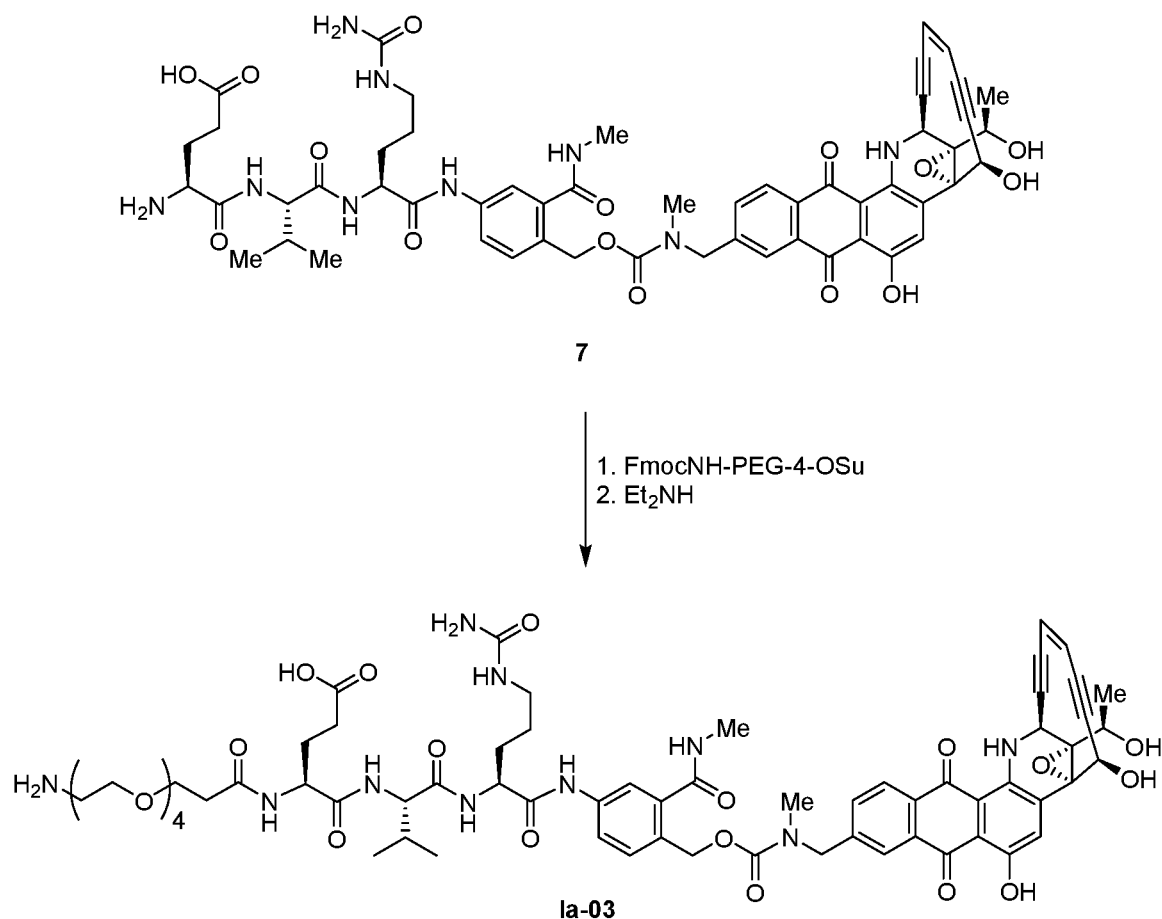

FIG. 1 confirms that ADCs made with a modified SI moiety as disclosed herein are efficacious in anticancer treatment, in mouse model using H226 (mesothelioma) cancer cells, which express mesothelin but not CD70. The graph shows that an ADC made with compound (Ia-03) and an anti-mesothelin monoclonal antibody (Terrett et al., U.S. Pat. No. 8,268,970 B2 (2012)) reduced the tumor volume after 35 days, compared to controls consisting of either formulation buffer or an ADC made with compound (Ia-03) and an anti-CD70 monoclonal antibody (Terrett et al., U.S. Pat. No. 8,124,738 B2 (2012)). In the anti-CD70 ADC, the absence of expression of the CD70 antigen by the H226 cells prevents the anti-CD70 antibody from being an effective targeting agent for the ADC. (Both the anti-mesothelin and anti-CD70 were modified with an N297A substitution to make them suitable amine acceptors for a transglutaminase-mediated conjugation.)

Example 4—Preparation of Conjugates by Maleimide Michael Addition

This general procedure is based on introduction of free thiol groups into an antibody by reaction of lysine 8-amino groups with 2-iminothiolane, followed by reaction with a maleimide-containing linker moiety, such as compounds Ia-01 and Ib-05. Initially the antibody is buffer exchanged into 0.1 M phosphate buffer (pH 8.0) containing 50 mM NaCl and 2 mM DTPA and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at room temperature, the antibody is desalted into 50 mM HEPES, 5 mM Glycine, 2 mM DTPA, pH 5.5 using a SEPHADEX™ G-25 column and the number of thiol groups introduced determined rapidly by reaction with DTDP. Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at RT. Blank samples of buffer alone plus DTDP are also incubated alongside. After 10 min, absorbance at 324 nm is measured and the number of thiol groups is quantitated using an extinction coefficient for thiopyridine of 19,800 $M^{-1}$.

Typically a thiolation level of about two to three thiol groups per antibody is achieved. For example, with some antibodies this can be achieved by adding a 15-fold molar excess of 2-iminothiolane followed by incubation at RT for 1 h. The antibody is then incubated with 2-iminothiolane at the desired molar ratio and then desalted into conjugation buffer (50 mM HEPES, 5 mM glycine, 2 mM DTPA, pH 5.5)). The thiolated material is maintained on ice while the number of thiols introduced is quantitated as described above.

After verification of the number of thiols introduced, the drug-linker moiety is added at a 2.5-fold molar excess per thiol. The conjugation reaction is allowed to proceed in conjugation buffer containing a final concentration of 25% propylene glycol and 5% trehalose. Commonly, the linker stock solution is dissolved in 100% DMSO. The stock solution is added directly to the thiolated antibody.

The conjugation reaction mixture is incubated at RT for 2 h with gentle stirring. A 10-fold molar excess of N-ethyl maleimide (100 mM Stock in DMSO) is then added to the conjugation mixture and stirred for an additional hour to block any unreacted thiols. The sample is then filtered via a 0.2μ filter The material is buffer exchanged via TFF Viva-Flow 50 Sartorius 30 MWCO PES membrane into 10 mg/mL glycine, 20 mg/mL sorbitol, 15% acetonitrile, pH 5.0 (5×TFF buffer exchange volume), to remove any unreacted drug. The final formulation is carried out by TFF into 20 mg/mL sorbitol, 10 mg/mL glycine, pH 5.0.

Example 5—Mouse Model Testing

The following procedure can be used for mouse model testing of the type reported in FIG. 1.

Cancer cells (H226 mesothelioma in the instance of FIG. 1), resuspended in 0.1 mL phosphate buffered saline ("PBS") plus 0.1 mL matrigel, are implanted subcutaneously at the flank region of SCID mice. Tumor measurements are started 28 days later, and mice are randomized into groups of 7 mice, each with roughly the same tumor size (in $mm^3$ estimated by LWH/2 of tumors; approximately 135 $mm^3$ in the instance on FIG. 1). At 29 days post tumor implantation, mice are dosed intraperitoneally singly with testing conjugate.

Example 6—Synthesis of Compounds Via Scheme A

This Example and FIGS. 1A-1B relate to Scheme A for the synthesis of compounds disclosed herein, with particular reference to compound Ia-03.

Compound 2. A mixture of 6-aminoisobenzofuran-1(3H)-one 1 (1.0 g, 6.70 mmol) and methanamine (2M in MeOH, 16.76 mL, 33.5 mmol) in DCM (5 mL) was stirred for 3 days. LCMS (M+H−H$_2$O=163.0) showed the presence of ring-opened product. The solvent was evaporated to obtain compound 2 as a colorless paste (quantitative yield).

Compound 3. To a solution of (S)-2-((S)-2-((((9H-fluoren-9-yl)methoxy)carbonyl)-amino)-3-methylbutanamido)-5-ureidopentanoic acid (Fmoc-Val-Cit, 1.681 g, 3.39 mmol) and compound 2 (1.22 g, 6.77 mmol) in THF (5 mL) was added EEDQ (1.674 g, 6.77 mmol). The reaction mixture was stirred at RT overnight. LCMS (M+H−H$_2$O=659.3) showed product formation. The reaction was directly purified on a COMBIFLASH™ column using 40 g silical gel and eluting with 0-100% MeOH/DCM to yield compound 3 (53% yield).

Compound 4. To a solution of compound 3 (206 mg, 0.313 mmol) in DMF (1 mL) was added bis(4-nitrophenyl) carbonate (190 mg, 0.625 mmol) followed by DIEA (0.164 mL, 0.938 mmol). The reaction was stirred at RT for 3 h, after which LCMS (M+H=824.3) showed product formation. It was directly injected into a COMBIFLASH™ column (40 g silica gel) and eluted with 0-100% MeOH/DCM to yield compound 4 as white solid (50% yield).

Compound 6. To a solution of compound 5 (26 mg, 0.054 mmol) in DMF (0.5 mL) was added compound 4 (66.6 mg, 0.081 mmol) followed by 2,6-lutidine (0.013 mL, 0.108 mmol). The reaction was stirred at RT for 3 h after which LCMS (M+H=1167.3) showed completion of the reaction to form an intermediate adduct. The reaction was worked up with saturated aqueous NaHCO$_3$/EtOAc and the adduct was taken in crude form to next step.

To a solution of the adduct (63.0 mg, 0.054 mmol) in DMF (0.5 mL) was added DEA (0.056 mL, 0.540 mmol). LCMS (M+H=945.4) after 30 min showed completion of the reaction. The reaction mixture was diluted with DMSO (0.5 ml) and purified on a Shimadzu LC-20AP preparative HPLC with XBridge Prep C18 5 μm OBD 10×150 mm column eluting with 0-95% H$_2$O/acetonitrile (0.05% formic acid). The product containing fraction at 11 min was lyophilized to afford compound 6 as a purple solid.

Compound 7. A mixture of (S)-2-((((9H-fluoren-9-yl)methoxy)carbonyl)amino)-5-(allyloxy)-5-oxopentanoic acid (FmocNH—O-alloc-Glu, 38.1 mg, 0.093 mmol) and compound 6 (88 mg, 0.093 mmol) was treated with 2,6-lutidine (0.033 mL, 0.279 mmol) and HATU (70.8 mg, 0.186 mmol) and stirred for 1 h. LCMS (M+H=1279.6) showed the formation of an adduct. The reaction was worked up with EtOAc/saturated aqueous NaHCO$_3$ and the adduct was taken in crude form to next step.

To the adduct from above step was added morpholine (0.016 mL, 0.186 mmol) followed by palladiumtetrakis (10.76 mg, 9.31 μmol) and stirred for 30 min. LCMS (M+H=1240.0) shows the removal of the alloc group. To this mixture was added DEA (0.049 mL, 0.466 mmol) and stirred for 30 min after which LCMS (M+H=1017.6) showed completion of the reaction. The reaction was purified on a reverse-phase COMBIFLASH™ column (40 g c-18) eluting with 0-100% water in acetonitrile (0.05% formic acid) to provide compound 7 as a purple solid.

Compound Ia-03. A solution of compound 7 (10.2 mg, 9.50 μmol) and 2,5-dioxopyrrolidin-1-yl 1-(9H-fluoren-9-yl)-3-oxo-2,7,10,13,16-pentaoxa-4-azanonadecan-19-oate (FmocNH-PEG4-OSuc, 5.55 mg, 9.50 μmol) in DMF (0.5 mL) was treated with 2,6-lutidine (3.32 μl, 0.028 mmol) and stirred for 3 h. LCMS (M+H=1357.5) showed completion of the reaction. To this reaction was added DEA (0.020 mL, 0.190 mmol), followed by stirring for 30 min after which LCMS (M+H=1135.4) showed the completion of reaction. The reaction mixture was diluted with DMSO (0.5 mL) and purified on a Shimadzu LC-20AP preparative HPLC with XBridge Prep C18 5 mm OBD 10×150 mm column eluting with 0-95% H$_2$O/acetonitrile (0.05% formic acid). The product containing fraction at 11.5 min was lyophilized to yield compound Ia-03 as a purple solid.

Following Scheme A, mutatis mutandis, the compounds in Table D were prepared:

TABLE D

Compounds Made per Scheme A

| Compound | Expected Mass (M + H) | Observed Mass (M + H) |
|---|---|---|
| Compound A | 1134.4 | 1135.4 |
| (Ia-01) | 1137.4 | 1138.4 |
| (Ia-02) | 1497.5 | 1498.9 |
| (Ia-03) | 1320.5 | 1321.3 |
| (Ia-04) | 1232.5 | 1233.3 |

Example 7—Synthesis of Compounds Via Scheme B

This Example and FIGS. 3A-3C relate to Scheme B for the synthesis of compounds disclosed herein, with particular reference to compounds Ia-06 and Ia-09.

Compound 8. To a solution of 6-aminoisobenzofuran-1 (3H)-one 1 (1 g, 6.70 mmol) in methanol (1 mL) was added ethane-1,2-diamine (2.246 mL, 33.5 mmol). The reaction mixture was stirred at RT for 3 h. LCMS (M+H−H$_2$O=192.2) showed the disappearance of starting material and the presence of product. The solvent and the excess reagent was removed by evaporation and the crude 8 was taken to next step.

Compound 9. To a solution of compound 8 (1402 mg, 6.70 mmol) in DMF (5 mL) at 0° C. was added a solution of allyl chloroformate (0.715 mL, 6.70 mmol) in THF (1 mL). The reaction was stirred for 1 h after which LCMS (M+H−H$_2$O=276.2) showed the formation of product. The reaction was quenched by the addition of saturated aqueous NaHCO$_3$ and extracted with EtOAc. The crude product was purified on a 40 g silica gel column, eluting with 0-100% MeOH in DCM to yield compound 9 as white solid.

Compound 10. To a solution of (S)-2-((S)-2-((((9H-fluoren-9-yl)methoxy)carbonyl)amino)-3-methylbutanamido)-5-ureidopentanoic acid (Fmoc-Val-Cit, 242 mg, 0.488 mmol) and compound 9 (286 mg, 0.975 mmol) in MeOH (2 mL) was added EEDQ (241 mg, 0.975 mmol). The reaction mixture was stirred at RT overnight. LCMS (M+H=772.5) showed a new peak. The reaction was directly purified on a COMBIFLASH™ column using 40 g silical gel eluting with 0-100% MeOH/DCM to yield compound 10.

Compound 11. To a solution of compound 10 (102 mg, 0.132 mmol) in DMF (1 mL) was added bis(4-nitrophenyl) carbonate (121 mg, 0.396 mmol) and DIPEA (0.046 mL, 0.264 mmol). The reaction was stirred at RT for 3 h, after which LCMS (M+H=937.3) showed completion of the reaction. Direct purification on a COMBIFLASH™ apparatus on a 40 g silica gel column eluting with 0-50% MeOH in DCM yielded compound 11 as a white solid.

Compound 12. A mixture of compound 11 and compound 5 (53.0 mg, 0.110 mmol) was stirred overnight. LCMS (M+H=1110.4) showed completion of the reaction, which was worked up with saturated aqueous $NaHCO_3$/EtOAc and dried. To this crude mixture in DMF (5 mL) was added DEA (0.057 mL, 0.550 mmol) followed by stirring for 30 min. LCMS (M+H=888.1) showed completion of the reaction. The product was directly injected into a reverse phase COMBIFLASH™ column (150 g C-18) and eluted with 0-50% water in acetonitrile (0.05% formic acid) to obtain compound 12 as a purple solid.

Compound 13. To a solution of compound 12 (150 mg, 0.142 mmol) and 2,5-dioxopyrrolidin-1-yl 1-(9H-fluoren-9-yl)-3-oxo-2,7,10,13,16-pentaoxa-4-azanonadecan-19-oate (FmocNH-$PEG_4$-OSu, 83 mg, 0.142 mmol) in DMF (0.5 mL) was added 2,6-lutidine (0.050 mL, 0.425 mmol). The reaction mixture was stirred for 2 h. LCMS (M+H=1528.7) showed anew peak. The crude product was purified on reverse phase combiflash eluting with 0-100% acetonitrile/water (0.05% formic acid) to yield the desired product as purple solid.

The product from previous step (5 mg, 0.037 µmol) was dissolved in DMF (0.5 mL) and treated with phenylsilane (0.775 µl, 6.28 µmol) followed by palladiumtetrakis (1.815 mg, 1.571 µmol). LCMS (M+H=1444.4) shows the removal of the alloc group. The reaction was filtered through a syringe filter and solvent was evaporated to give compound 13.

Compound Ia-09. A solution of 8 (4.8 mg, 3.14 µmol) was dissolved in DMF (0.5 mL) and treated with 2,5,8,11,14,17,20,23-octaoxahexacosan-26-oic acid (6.75 mg, 0.016 mmol), HATU (6.22 mg, 0.016 mmol) and 2,6-lutidine (4 µL, 0.033 mmol) and stirred for 1 h after which acylation of the amine. The crude reaction was then treated with DEA (3.28 µl, 0.031 mmol). LCMS (M+H=1616.5) shows the deprotectin of the Fmoc group. The crude product was directly injected into Shimadzu prep HPLC with xBridge PrepC18 5☐ 19×150 mm column and eluted with 0-95% MeCN/H2O (0.1% FA) and the product containing fractions were lyophilized to provide compound Ia-09 (1.3 mg, 0.833 µmol, 26.5% yield) as purple solid.

Compound 14. A solution of compound 12 in DMF (0.5 mL) was treated with 2,6-lutidine (10.24 µl, 0.088 mmol) followed by acetic anhydride (2.76 µl, 0.029 mmol). LCMS LCMS (M+H=1100.3) after 5 min shows the completion of acetylation. To this mixture was added morpholine (5.10 µl, 0.059 mmol) followed by palladiumtetrakis (6.77 mg, 5.86 µmol) and stirred for 1 h. LCMS (M+H=1016.3) showed completion of the reaction. The reaction was directly purified on a reverse phase COMBIFLASH™ unit using a 50 g C-18 column eluting with 0-50% water/acetonitrile (0.05% formic acid) to yield compound 14 as a purple solid.

Compound Ia-06. To a solution of compound 14 (22 mg, 0.022 mmol) in DMF (0.5 mL) was added 2,5-dioxopyrrolidin-1-yl 1-(9H-fluoren-9-yl)-3-oxo-2,7,10,13,16-pentaoxa-4-azanonadecan-19-oate (12.66 mg, 0.022 mmol) and 2,6-lutidine (7.57 µl, 0.065 mmol). The reaction was stirred for 1 h, after which LCMS showed completion of the reaction. Diethylamine (0.011 mL, 0.108 mmol) was added and the reaction mixture was stirred for 30 min, after which LCMS (M+H=1363.3) showed the formation of product. The reaction was diluted with DMSO (0.5 mL) and purified on a Shimadzu LC-20AP preparative HPLC with XBridge Prep C18 5D m OBD 10×150 mm column eluting with 0-95% H2O/acetonitrile (0.05% formic acid). The product containing fractions were lyophilized to obtain compound Ia-06 as a purple solid.

Following Scheme B, mutatis mutandis, the compounds in Table E were prepared:

TABLE E

Compounds Made per Scheme B

| Compound | Expected Mass (M + H) | Observed Mass (M + H) |
| --- | --- | --- |
| (Ia-05) | 1220.5 | 1221.2 |
| (Ia-06) | 1262.5 | 1263.3 |
| (Ia-07) | 1262.5 | 1264.5 |
| (Ia-08) | 1324.5 | 1326.2 |
| (Ia-09) | 1614.7 | 1616.5 |
| (Ia-10) | 1790.8 | 896.6 (M + H)/2 |
| (Ia-11) | 2319.1 | 1161.3 (M + H)/2 |

Example 8—Synthesis of Compounds Via Scheme C

This Example and FIG. 4 relate to Scheme C for the synthesis of compounds disclosed herein, with particular reference to compound Ib-05.

Compound 17. To a mixture of compound 15 (124 mg, 0.312 mmol) and compound 16 (310 mg, 0.312 mmol) in DMF (2 mL)/DMSO (2 mL) was added DIPEA (0.164 mL, 0.937 mmol). The reaction mixture was heated at 50° C. for 2 h. LCMS (M+H=1251.2) showed completion of the reaction. The base was evaporated and the crude product was purified on a COMBIFLASH™ column (80 g silica gel), eluting with 0-50% MeOH/DCM to yield compound 17 as a white solid.

Compound 18. A solution of compound 17 (52 mg, 0.042 mmol) in DMF (0.5 mL) was treated with morpholine (7.23 µl, 0.083 mmol), followed by palladiumtetrakis (9.60 mg, 8.30 µmol). LCMS after 1 h showed removal of the alloc group. This solution was treated with DEA (0.043 mL, 0.415 mmol). After 30 min, LCMS (M+H/2=495.9) showed completion of the reaction. The crude product was directly injected into a Shimadzu prep HPLC with xBridge PrepC18 5 mm 19×150 mm column and eluted with 0-95% acetonitrile/$H_2O$ (0.1% formic acid). The product containing fractions were lyophilized to give compound 18 as a white solid.

Compound Ib-05. A solution of compound 18 (17 mg, 0.017 mmol) and 2,5-dioxopyrrolidin-1-yl 6-(2,5-dioxo-2,5-dihydro-1H-pyrrol-1-yl)hexanoate (MC-OSuc, 5.29 mg, 0.017 mmol) in DMF (0.5 mL)/DMSO (0.5 mL) was treated with 2,6-lutidine (6.00 µl, 0.052 mmol) and heated at 40° C. for 1 h. LCMS (M+H=1183.3) showed completion of the reaction. The crude product was directly injected into a Shimadzu prep HPLC with xBridge PrepC18 5 mm 19×150 mm column and eluted with 0-95% acetonitrile/$H_2O$ (0.1% formic acid). The product containing fractions were lyophilized to give 15 mg of compound Ib-05 as a white solid.

Compound B was also synthesized by Scheme C, mutatis mutandis (mass spec (M+H) 1182.5 expected, 1183.3 observed).

Example 9—Synthesis of Compounds Via Scheme D

This Example and FIG. 5 relate to Scheme D for the synthesis of compounds disclosed herein, with particular reference to compound Ib-01.

Compound 21. A solution of compound 20 (575 mg, 0.604 mmol) and compound 19 (240 mg, 0.604 mmol) in DMF (1 mL) was treated with DIPEA (0.316 mL, 1.811 mmol). After stirring at RT for 3 h, LCMS (M+H=1211.0) showed completion of the reaction. The base was evaporated and the crude product was purified on a COMBIFLASH™ column using 80 g silica gel, eluting with 0-50% MeOH/DCM to yield compound 21 as a pale yellow solid.

Compound 22. A solution of compound 21 (0.206 g, 0.170 mmol) in DMF (1 mL) was treated with DEA (1 mL) and stirred for 1 h. The excess base was evaporated and the solution was treated with a solution of HATU (0.071 g, 0.187 mmol) and 1-(9H-fluoren-9-yl)-3-oxo-2,7,10,13,16-pentaoxa-4-azanonadecan-19-oic acid (0.083 g, 0.170 mmol), and 2,6-lutidine (0.059 mL, 0.510 mmol). After stirring for 30 min, LCMS (M+H=1458.4) showed completion of the reaction. The reaction purified on a reverse phase COMBIFLASH™ unit using 50 g column, eluting with 0-100% acetonitrile/$H_2O$ (0.05% formic acid) to afford compound 22.

Compound Ib-01. A solution of compound 22 (0.249 g) was treated with TFA (1 mL) and stirred for 1 h, after which LCMS (M+H=1358.1) showed removal of the Boc protecting group. The TFA was evaporated with a V-10 evaporator.

In a vial, 2,5,8,11,14,17,20,23-octaoxahexacosan-26-oic acid (0.070 g, 0.171 mmol) was dissolved in DMF (0.5 mL) and treated with HATU (0.078 g, 0.205 mmol) and DIPEA (0.149 mL, 0.854 mmol) and stirred for 20 min. This solution was treated with deprotected compound 22 and stirred for 30 min LCMS LCMS (M+H=1752.4) showed the formation of the desired product.

This solution was treated with DEA (0.357 mL, 3.41 mmol). LCMS (M+H=1529.3) after 30 min shows the formation of compound Ib-01. The base was evaporated in a V-10 evaporator and the crude product was purified on a reverse phase COMBIFLASH™ unit using a 50 g C-18 column and eluted with 0-95% acetonitrile/$H_2O$ (0.1% formic acid) and the product containing fractions were lyophilized to give compound Ib-01 (122 mg, 0.073 mmol, 43.0% yield).

Following Scheme D mutatis mutandis, the compounds in Table F were prepared:

TABLE F

Compounds Made per Scheme D

| Compound | Expected Mass (M + H) | Observed Mass (M + H) |
|---|---|---|
| (Ib-01) | 1528.8 | 1529.3 |
| (Ib-02) | 1148.5 | 575.5 (M + H)/2 |
| (Ib-03) | 1237.5 | 1237.4 |
| (Ib-04) | 1412.7 | 1413.5 |

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

Acronyms and Abbreviations

This is a list of acronyms and abbreviations used in this specification, along with their meanings.

| ACRONYM OR ABBREVIATION | MEANING OR DEFINITION |
|---|---|
| Alloc | Allyloxycarbonyl |
| Boc | t-Butyloxycarbonyl |
| DCM | Dichloromethane |
| DEA | Diethylamine |
| DIPEA, DIEA | N,N-diisopropylethylamine, also known as Hünig's base |
| DMF | N,N-dimethylformamide |
| DMSO | Dimethyl sulfoxide |
| DTDP | 2,2'-dithiodipyridine |
| DTPA | Diethylenetriaminepentaacetic acid |
| EEDQ | Ethyl 2-ethoxyquinoline-1(2H)-carboxylate |
| Fmoc | Fluorenylmethyloxycarbonyl |
| HATU | Hexafluorophosphate Azabenzotriazole Tetramethyl Uronium; 1-[Bis(dimethylamino)-methylene]-1H-1,2,3-triazolo[4,5-b]pyridinium 3-oxide hexafluorophosphate |
| HEPES | 4-(2-Hydroxyethyl)piperazine-1-ethanesulfonic acid, N-(2-Hydroxyethyl)piperazine-N'-(2-ethanesulfonic acid) |
| PEG | Poly(ethylene glycol) |
| RT | Room temperature, circa 25° C. |
| TFA | Trifluoroacetic acid |
| THF | Tetrahydrofuran |

REFERENCES

Full citations for the following references cited in abbreviated fashion by first author (or inventor) and date earlier in this specification are provided below. Each of these references is incorporated herein by reference for all purposes.

Alouane et al., *Ang. Chem. Int. Ed.* 2015, 54, 7492, "Self-Immolative spacers: Kinetic Aspects, Structure-Property Relationships, and Application."

Boyd et al., U.S. Pat. No. 7,691,962 B2 (2010).

Burke et al., US 2017/0247412 A1 (2017).

Carl et al., *J. Med. Chem.* 1981, 24(5), 479, "A Novel Connector Linkage Applicable in Prodrug Design." [1981a]

Carl et al., WO 81/01145 A1 (1981). [1981b]

Doronina et al., *Bioconjugate Chem.* 2008, 19, 1960, "Novel Peptide Linkers for Highly Potent Antibody-Auristatin Conjugate."

Dorywalska et al., *Mol. Cancer Ther.* 2016, 15(5), 958, "Molecular Basis of Valine-citrulline-PABC Linker Instability in Site-specific ADCs and its Mitigation by Linker Design."

Dubowchik et al., Biorg. Med. Chem. Lett. 1998, 8, 3341, "Cathepsin B-Sensitive Dipeptide Prodrugs. 1. A Model Study of Structural Requirements for Efficient Release of Doxorubicin." [1998a].

Dubowchik et al., Bioorg. Med. Chem. Lett. 1998, 8, 3347, "Cathepsin B-Sensitive Dipeptide Prodrugs. 2. Models of Anticancer Drugs Paclitaxel (Taxol®), Mitomycin C and Doxorubicin." [1998b].

Dubowchik et al., *Bioconjugate Chem.* 2002, 13, 855, "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity."

Feng, U.S. Pat. No. 7,375,078 B2 (2008).

Feng, U.S. Pat. No. 7,989,434 B2 (2011).

Firestone et al., U.S. Pat. No. 6,214,345 B1 (2001).

Gerber et al., *Nat. Prod. Rep.* 2013, 30, 625, "The antibody-drug conjugate: an enabling modality for natural product based cancer therapies."

Jeffrey, U.S. Pat. No. 8,039,273 (2011).

Jeffrey et al., *Bioconjugate Chem.* 2006, 17, 831, "Development and Properties of 3-Glucuronide Linkers for Monoclonal Antibody-Drug Conjugates."

Lin et al., U.S. Pat. No. 9,089,614 B2 (2015).

Kim et al., US 2016/0184451 A1 (2016).

Kim et al., US 2017/0095576 A1 (2017).

Machida et al., *Angew. Chem. Int. Ed.* 2016, 55, 8595, "Allosterically Regulated Phosphatase Activity from Peptide-PNA Conjugates Folded Through Hybridization."

Major et al., *Chem. Commun.* 2011, 47, 7968, "Investigation of Self-Immolative Linkers in the Design of Hydrogen Peroxide Activated Metalloprotein Inhibitors."

McDonagh et al., WO 2007/103288 A2 (2007).

Senter et al., U.S. Pat. No. 7,091,186 B2 (2006).

Szczepanik et al., U.S. Pat. No. 8,828,678 B2 (2014).

Zhang et al., *Chem. Commun.* 2015, 51, 7031, "An Enzyme Activatable Probe with a Self-immolative Linker for Rapid and Sensitive Alkaline Phosphatase Detection and Cell Imaging through a Cascade Reaction."

What is claimed is:

1. A compound represented by formula (I)

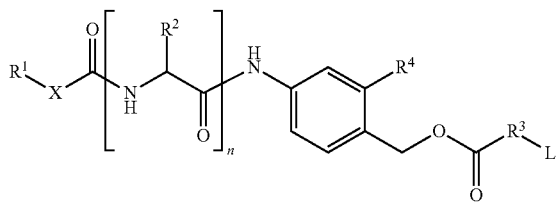

(I)

wherein $R^1$ is $C_1$-$C_5$ alkyl, $N_3$, OH, SH, $ONH_2$, $NH_2$, $CO_2H$,

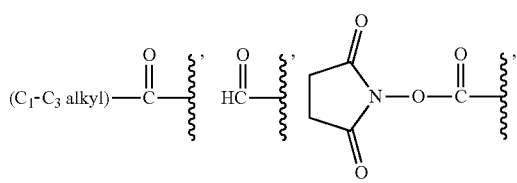

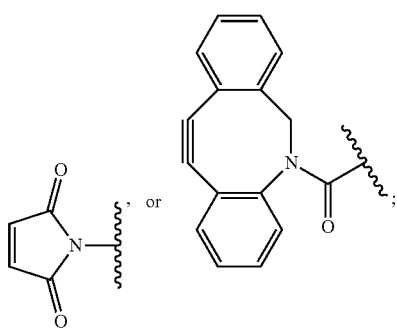

$R^2$ is the side chain residue of an amino acid selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

n is 2 3, 4, or 5;

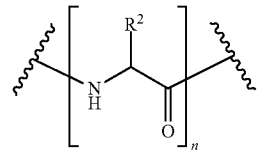

comprising a polypeptide whose bond to

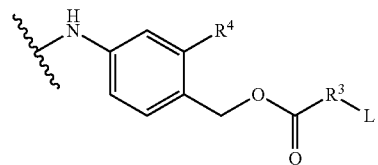

is cleavable by cathepsin B;

$R^3$ is NH,

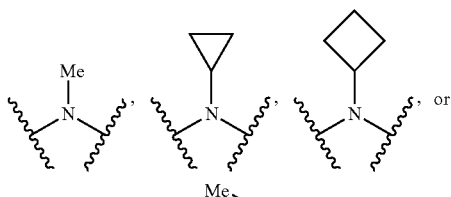

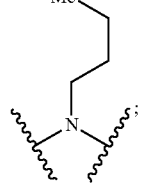

R⁴ is

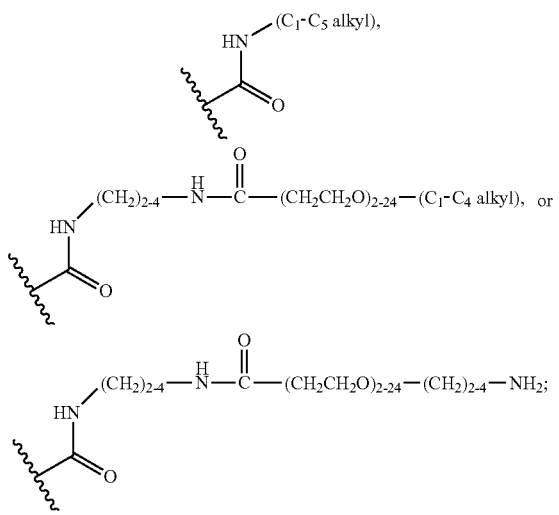

L is the residue of a bioactive molecule of the formula L-R³H; and

X is spacer group.

2. A compound according to claim 1, wherein

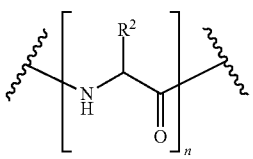

is Val-Cit, Glu-Val-Cit, Phe-Lys, Phe-Arg, Val-Lys, Ala-Lys, Phe-Phe-Lys, Gly-Phe-Lys, Val-Ala, Ala-Val-Cit, or Val-Gly.

3. A compound according to claim 1, wherein R¹ is NH₂ or

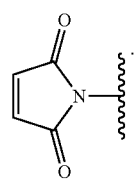 [SMILES: *N1C(=O)C=CC1=O]

4. A compound according to claim 1, wherein R⁴ is

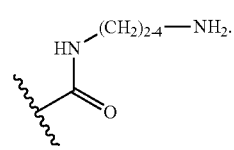

5. A compound according to claim 1, wherein R⁴ is

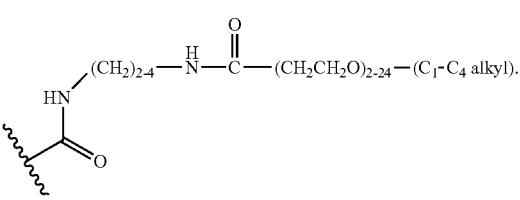

6. A compound according to claim 1, wherein R⁴ is

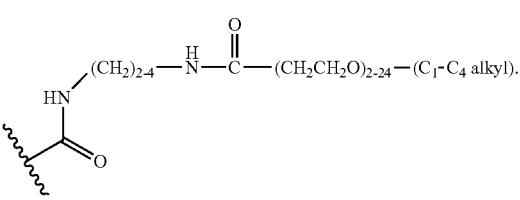

* * * * *